(12) United States Patent
Sappey

(10) Patent No.: US 9,354,177 B2
(45) Date of Patent: May 31, 2016

(54) SYSTEM AND METHOD FOR DEFECT DETECTION AND PHOTOLUMINESCENCE MEASUREMENT OF A SAMPLE

(71) Applicant: KLA-Tencor Corporation, Milpitas, CA (US)

(72) Inventor: Romain Sappey, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/212,496

(22) Filed: Mar. 14, 2014

(65) Prior Publication Data

US 2015/0001421 A1 Jan. 1, 2015

Related U.S. Application Data

(60) Provisional application No. 61/839,494, filed on Jun. 26, 2013.

(51) Int. Cl.
*G01N 21/64* (2006.01)
*G01N 21/88* (2006.01)

(52) U.S. Cl.
CPC ........ *G01N 21/6489* (2013.01); *G01N 21/8806* (2013.01); *G01N 2021/6495* (2013.01); *G01N 2021/8845* (2013.01); *G01N 2201/0662* (2013.01); *G01N 2201/06113* (2013.01)

(58) Field of Classification Search
CPC ............................... G01N 21/64; G01N 21/88
See application file for complete search history.

(56) References Cited

U.S. PATENT DOCUMENTS

| | | | |
|---|---|---|---|
| 6,201,601 B1 | 3/2001 | Vaez-Iravani et al. | |
| 7,504,642 B2 * | 3/2009 | Hummel et al. | 250/458.1 |
| 7,907,269 B2 | 3/2011 | Meeks | |
| 8,891,079 B2 * | 11/2014 | Zhao et al. | 356/237.2 |

(Continued)

FOREIGN PATENT DOCUMENTS

| | | |
|---|---|---|
| JP | 2006147848 A | 6/2006 |
| JP | 2010109156 A | 5/2010 |

OTHER PUBLICATIONS

Feng et al., "Characterization of stacking faults in 4H-Si C epilayers by room-temperature microphotoluminescence mapping," Applied Physics Letters, vol. 92, Issue 22, Jun. 3, 2008, pp. 221906-1-221906-3, Published by AIP Publishing, US.

*Primary Examiner* — David Porta
*Assistant Examiner* — Faye Boosalis
(74) *Attorney, Agent, or Firm* — Suiter Swantz pc llo

(57) ABSTRACT

Defect detection and photoluminescence measurement of a sample directing a beam of oblique-illumination wavelength light onto a portion of the sample, directing a beam of normal-illumination wavelength light for causing one or more photoluminescing defects of the sample to emit photoluminescent light onto a portion of the sample, collecting defect scattered radiation or photoluminescence radiation from the sample, separating the radiation from the sample into a first portion of radiation in the visible spectrum, a second portion of radiation including the normal-illumination wavelength light, and at least a third portion of radiation including the oblique-illumination wavelength light, measuring one or more characteristics of the first portion, the second portion or the third portion of radiation; detecting one or more photoluminescence defects or one or more scattering defects based on the measured one or more characteristics of the first portion, the second portion or the third portion of radiation.

62 Claims, 15 Drawing Sheets

(56) References Cited

U.S. PATENT DOCUMENTS

| | | |
|---|---|---|
| 2004/0092042 A1 | 5/2004 | Higgs |
| 2010/0182602 A1 * | 7/2010 | Urano ............... G01N 21/4738 356/369 |
| 2012/0049085 A1 | 3/2012 | Sappey et al. |
| 2012/0293793 A1 | 11/2012 | Uchino et al. |
| 2013/0016346 A1 | 1/2013 | Romanovsky et al. |

* cited by examiner

SYSTEM AND METHOD FOR DEFECT DETECTION AND PHOTOLUMINESCENCE MEASUREMENT OF A SAMPLE

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled PHOTOLUMINESCENCE AND DEFECT INSPECTION SYSTEMS AND METHODS, naming ROMAIN SAPPEY as inventor, filed Jun. 26, 2013, Application Ser. No. 61/839,494.

TECHNICAL FIELD

The present invention generally relates to the detection and classification of defects, in particular, the present invention relates to the detection and classification of photoluminescence and scattering defects.

BACKGROUND

As demand for ever-shrinking semiconductor devices continues to increase, so too will the demand for improved inspection tools for defect identification and classification. Defects impacting the quality of fabricated devices may include, for example, stacking fault defects and basal plane dislocation defects. Stacking fault defects and basal plane dislocations display a weak photoluminescent signature when stimulated with ultraviolet light. Current inspection tools do not efficiently measure photoluminescent defects in conjunction with scattering-type defects. As such, it is desirable to provide improved methods and systems that act to cure the defects of the prior art.

SUMMARY OF THE INVENTION

A system for defect detection and photoluminescence measurement of a sample is disclosed. In one aspect, the system may include, but is not limited to, an oblique-incidence radiation source configured to direct a beam of light of an oblique-illumination wavelength onto a portion of the sample along a direction oblique to the surface of the sample; a normal-incidence radiation source configured to direct a beam of light of a normal-illumination wavelength different from the oblique-illumination wavelength onto a portion of the sample along a direction substantially normal to the surface of the sample, wherein the beam of light of the normal-illumination wavelength is suitable for causing one or more photoluminescing defects of the sample to emit photoluminescent light; a sample stage assembly configured to secure the sample and selectively actuate the sample in order to perform a scanning process with at least the oblique-incidence radiation source and the normal-incidence radiation source; a set of collection optics configured to collect radiation from the sample, the radiation from the sample including at least one of radiation elastically scattered by one or more defects of the sample or photoluminescence radiation emitted by the one or more photoluminescing defects of the sample; a filter sub-system configured to receive at least a portion of the radiation collected by the set of collection optics, wherein the filter sub-system is configured to separate the radiation from the sample into a first portion of radiation including one or more wavelengths in the visible or near-infrared spectrum associated with the light emitted by the one or more photoluminescing defects of the sample, a second portion of radiation including the normal-illumination wavelength, and at least a third portion of radiation including the oblique-illumination wavelength; a detection sub-system including a first sensor for measuring one or more characteristics of the first portion of radiation transmitted by the filter sub-system, a second sensor for measuring one or more characteristics of the second portion of radiation transmitted by the filter sub-system and at least a third sensor for measuring one or more characteristics of the third portion of radiation transmitted by the filter sub-system; and a controller communicatively coupled to the first sensor, the second sensor and the third sensor, the controller configured to: detect one or more scattering defects based on at least one of the one or more characteristics measured by the second sensor and the third sensor; and detect one or more photoluminescence defects based on at least one of the one or more characteristics measured by the first sensor, the one or more characteristics measured by the second sensor and the one or more characteristics measured by the third sensor.

In another aspect, the system include, but is not limited to, an oblique-incidence radiation source configured to direct a beam of light of an oblique-illumination wavelength onto a portion of the sample along a direction oblique to the surface of the sample; a normal-incidence radiation source configured to direct a beam of light of a normal-illumination wavelength different from the oblique-illumination wavelength onto a portion of the sample along a direction substantially normal to the surface of the sample, wherein the beam of light of the normal-illumination wavelength is suitable for causing one or more photoluminescing defects of the sample to emit photoluminescent light; a sample stage assembly configured to secure the sample and selectively actuate the sample in order to perform a scanning process with at least the oblique-incidence radiation source and the normal-incidence radiation source; a set of collection optics configured to collect radiation from the sample, the radiation from the sample including at least one of radiation elastically scattered by one or more defects of the sample or photoluminescence radiation emitted by the one or more photoluminescing defects of the sample; a filter sub-system configured to receive at least a portion of the radiation collected by the set of collection optics, wherein the filter sub-system is configured to separate the radiation from the sample into a first portion of radiation including one or more wavelengths in the visible or near-infrared spectrum associated with the light emitted by the one or more photoluminescing defects of the sample, a second portion of radiation including the normal-illumination wavelength, a third portion of radiation including the oblique-illumination wavelength and at least a fourth portion of radiation including one or more wavelengths in the ultraviolet spectrum associated with the photoluminescent light emitted by the one or more photoluminescing defects of the sample; a detection sub-system including a first sensor for measuring one or more characteristics of the first portion of radiation transmitted by the filter sub-system, a second sensor for measuring one or more characteristics of the second portion of radiation transmitted by the filter sub-system, a third sensor for measuring one or more characteristics of the third portion of radiation transmitted by the filter sub-system and at least a fourth sensor for measuring one or more characteristics of the fourth portion of radiation transmitted by the filter sub-system; and a controller communicatively coupled to the first sensor, the second sensor and the third sensor, the controller configured to: detect one or more scattering defects based on the light measured by at least one of the second sensor and the third sensor; and detect one or more photoluminescence defects based on the light detected by at least one of the first sensor, the second sensor, the third sensor and the fourth sensor by comparing a signal from at least one of the first sensor, the second sensor, the third sensor and the fourth sensor in an area of the sample absent of photoluminescing defects to a signal from at least one of the first sensor, the second sensor, the third sensor and the fourth sensor acquired from a measured region of the sample.

In another aspect, the system include, but is not limited to, a normal-incidence radiation source configured to direct a beam of light of a normal-illumination wavelength onto a portion of the sample along a direction substantially normal to the surface of the sample, wherein the beam of light of the normal-illumination wavelength is suitable for causing one or more photoluminescing defects of the sample to emit photoluminescent light; a sample stage assembly configured to secure the sample and selectively actuate the sample in order to perform a scanning process with at least the oblique-incidence radiation source and the normal-incidence radiation source; a set of collection optics configured to collect radiation from the sample, the radiation from the sample including at least one of radiation elastically scattered by one or more defects of the sample or photoluminescence radiation emitted by the one or more photoluminescing defects of the sample; a filter sub-system configured to receive at least a portion of the radiation collected by the set of collection optics, wherein the filter sub-system is configured to separate the radiation from the sample into a first portion of radiation including one or more wavelengths in the visible or near-infrared spectrum associated with the light emitted by the one or more photoluminescing defects of the sample, a second portion of radiation including the normal-illumination wavelength, and at least a third portion of radiation including one or more wavelengths in the ultraviolet spectrum associated with the light emitted by the one or more photoluminescing defects of the sample; a detection sub-system including a first sensor for measuring one or more characteristics of the first portion of radiation transmitted by the filter sub-system, a second sensor for measuring one or more characteristics of the second portion of radiation transmitted by the filter sub-system and at least a third sensor for measuring one or more characteristics of the third portion of radiation transmitted by the filter sub-system; and a controller communicatively coupled to the first sensor, the second sensor and the third sensor, the controller configured to: detect one or more scattering defects based on the light measured by the second sensor; and detect one or more photoluminescence defects based on the light detected by at least one of the first sensor and the third sensor by comparing a signal from at least one of the first sensor and the third sensor in an area of the sample absent of photoluminescing defects to a signal from at least one of the first sensor and the third sensor acquired from a measured region of the sample.

In another aspect, the system include, but is not limited to, a normal-incidence radiation source configured to direct a beam of light of a normal-illumination wavelength onto a portion of the sample along a direction substantially normal to the surface of the sample, wherein the beam of light of the normal-illumination wavelength is suitable for causing one or more photoluminescing defects of the sample to emit photoluminescent light; a sample stage assembly configured to secure the sample and selectively actuate the sample in order to perform a scanning process with at least the oblique-incidence radiation source and the normal-incidence radiation source; a set of collection optics configured to collect radiation from the sample, the radiation from the sample including at least one of radiation elastically scattered by one or more defects of the sample or photoluminescence radiation emitted by the one or more photoluminescing defects of the sample; a filter sub-system configured to receive at least a portion of the radiation collected by the set of collection optics, wherein the filter sub-system is configured to separate the radiation from the sample into a plurality of portions of photoluminescent radiation, each portion including one or more wavelengths in a different spectral range of the radiation emitted by the one or more photoluminescing defects of the sample; a detection sub-system including a plurality of sensors, each sensor suitable for measuring one or more characteristics of one of the plurality of portions of photoluminescent radiation transmitted by the filter sub-system; and a controller communicatively coupled to each of the plurality of sensors, the controller configured to: detect one or more photoluminescence defects based on the light detected by each of the plurality of sensors by comparing a signal from at least one of the plurality of sensors in an area of the sample absent of photoluminescing defects to a signal from at least one the plurality of sensors acquired from a measured region of the sample; and classify the one or more detected photoluminescence defects based on one or more signals measured by each of the plurality of sensors.

A method for defect detection and photoluminescence measurement of a sample is disclosed. In one embodiment, the method may include, but is not limited to, directing a beam of oblique-illumination wavelength light onto a portion of the sample along a direction oblique to the surface of the sample; directing a beam of normal-illumination wavelength light onto a portion of the sample along a direction substantially normal to the surface of the sample, wherein the beam of light of the normal-illumination wavelength is suitable for causing one or more photoluminescing defects of the sample to emit photoluminescent light; collecting radiation from the sample, the radiation from the sample including at least one of radiation elastically scattered by one or more defects of the sample or photoluminescence radiation emitted by the one or more photoluminescing defects of the sample; separating the radiation from the sample into a first portion of radiation including one or more wavelengths in the visible spectrum associated with the light emitted by the one or more photoluminescing defects of the sample, a second portion of radiation including the normal-illumination wavelength light, and at least a third portion of radiation including the oblique-illumination wavelength light; measuring one or more characteristics of at least one of the first portion of radiation, the second portion of radiation and the third portion of radiation; detecting one or more scattering defects based on the measured one or more characteristics of at least one of the second portion of radiation and the third portion of radiation; and detecting one or more photoluminescence defects based on the measured one or more characteristics of at least one of the first portion of radiation, the second portion of radiation and the third portion of radiation by comparing the one or more characteristics of at least one of the first portion of radiation, the second portion of radiation and the third portion of radiation acquired from an area of the sample absent of photoluminescing defects to one or more characteristics of at least one of the first portion of radiation, the second portion of radiation and the third portion of radiation acquired from a measured region of the sample.

In another aspect, the method may include, but is not limited to, directing a beam of oblique-illumination wavelength light onto a portion of the sample along a direction oblique to the surface of the sample; directing a beam of normal-illumination wavelength light along a direction substantially normal to the surface of the sample, wherein the beam of light of the normal-illumination wavelength is suitable for causing one or more photoluminescing defects of the sample to emit photoluminescent light; collecting radiation from the sample, the radiation from the sample including at least one of radiation elastically scattered by one or more defects of the sample or photoluminescence radiation emitted by the one or more photoluminescing defects of the sample; separating the radiation from the sample into a first portion of radiation including one or more wavelengths in the visible or near-infrared spectrum associated with the light emitted by the one or more photoluminescing defects of the sample, a second portion of radiation including the normal-illumination wavelength, a third portion of radiation including the oblique-illumination wavelength and at least a fourth portion of radiation including one or more wavelengths in the ultraviolet spectrum associated with the photoluminescent light emitted by the one or more photoluminescing defects of the sample; measuring one or more characteristics of at least one of the first portion of radiation, one or more characteristics of the second portion of radiation, one or more characteristics of the third portion of radiation and one or more characteristics of the fourth portion of radiation; detecting one or more scattering defects based on the measured one or more characteristics of at least one of the second portion of radiation and the third portion of radiation; and detecting one or more photoluminescence defects based on the measured one or more characteristics of at least one of the first portion of radiation, the second portion of radiation, and the third portion of radiation by comparing the one or more characteristics of at least one of the first portion of radiation, the second portion of radiation, the third portion of radiation and the fourth portion of radiation acquired from an area of the sample absent of photoluminescing defects to one or more characteristics of at least one of the first portion of radiation, the second portion of radiation, the third portion of radiation and the fourth portion of radiation acquired from a measured region of the sample.

In another aspect, the method may include, but is not limited to, directing a beam of normal-illumination wavelength light along a direction substantially normal to the surface of the sample, wherein the beam of light of the normal-illumination wavelength is suitable for causing one or more photoluminescing defects of the sample to emit photoluminescent light; collecting radiation from the sample, the radiation from the sample including at least one of radiation elastically scattered by one or more defects of the sample or photoluminescence radiation emitted by the one or more photoluminescing defects of the sample; separating the radiation from the sample into a first portion of radiation including one or more wavelengths in the visible or near-infrared spectrum associated with the light emitted by the one or more photoluminescing defects of the sample, a second portion of radiation including the normal-illumination wavelength and at least a third portion of radiation including one or more wavelengths in the ultraviolet spectrum associated with the photoluminescent light emitted by the one or more photoluminescing defects of the sample; measuring one or more characteristics of at least one of the first portion of radiation, one or more characteristics of the second portion of radiation and one or more characteristics of the third portion of radiation; detecting one or more scattering defects based on the measured one or more characteristics of at least one of the second portion of radiation and the third portion of radiation; and detecting one or more photoluminescence defects based on the measured one or more characteristics of at least one of the first portion of radiation, the second portion of radiation, and the third portion of radiation by comparing the one or more characteristics of at least one of the first portion of radiation, the second portion of radiation and the third portion of radiation acquired from an area of the sample absent of photoluminescing defects to one or more characteristics of at least one of the first portion of radiation, the second portion of radiation and the third portion of radiation acquired from a measured region of the sample.

In another aspect, the method may include, but is not limited to, directing a beam of normal-illumination wavelength light onto a portion of the sample along a direction substantially normal to the surface of the sample, wherein the beam of light of the normal-illumination wavelength is suitable for causing one or more photoluminescing defects of the sample to emit photoluminescent light; collecting radiation from the sample, the radiation from the sample including at least one of radiation elastically scattered by one or more defects of the sample or photoluminescence radiation emitted by the one or more photoluminescing defects of the sample; separating the radiation from the sample into a plurality of portions of photoluminescent radiation, each portion including one or more wavelengths in a different spectral range of the light emitted by the one or more photoluminescing defects of the sample; measuring one or more characteristics of each of the plurality of portions of photoluminescent radiation; detecting one or more photoluminescence defects based on the measured one or more characteristics of each of the plurality of portions of photoluminescent radiation; and classifying the one or more detected photoluminescence defects based on one or more signals associated with each of the plurality of portions of photoluminescent radiation.

In another aspect, the method may include, but is not limited to, directing a beam of normal-illumination wavelength light onto a portion of the sample along a direction substantially normal to the surface of the sample, wherein the beam of light of the normal-illumination wavelength is suitable for causing one or more photoluminescing defects of the sample to emit photoluminescent light; directing a beam of oblique-illumination wavelength light onto a portion of the sample along a direction along a direction oblique to the surface of the sample; collecting radiation from the sample, the radiation from the sample including at least one of radiation elastically scattered by one or more defects of the sample or photoluminescence radiation emitted by the one or more photoluminescing defects of the sample; separating the radiation from the sample into a visible portion of photoluminescent radiation and a near ultraviolet (NUV) portion of photoluminescent radiation; measuring one or more characteristics of the visible portion of photoluminescent radiation and the NUV portion of photoluminescent radiation; detecting one or more photoluminescence defects based on the measured one or more characteristics of the visible portion of photoluminescent radiation and the NUV portion of photoluminescent radiation; and classifying the one or more detected photoluminescence defects based on one or more signals associated with the visible portion of photoluminescent radiation and the NUV portion of photoluminescent radiation.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1A:
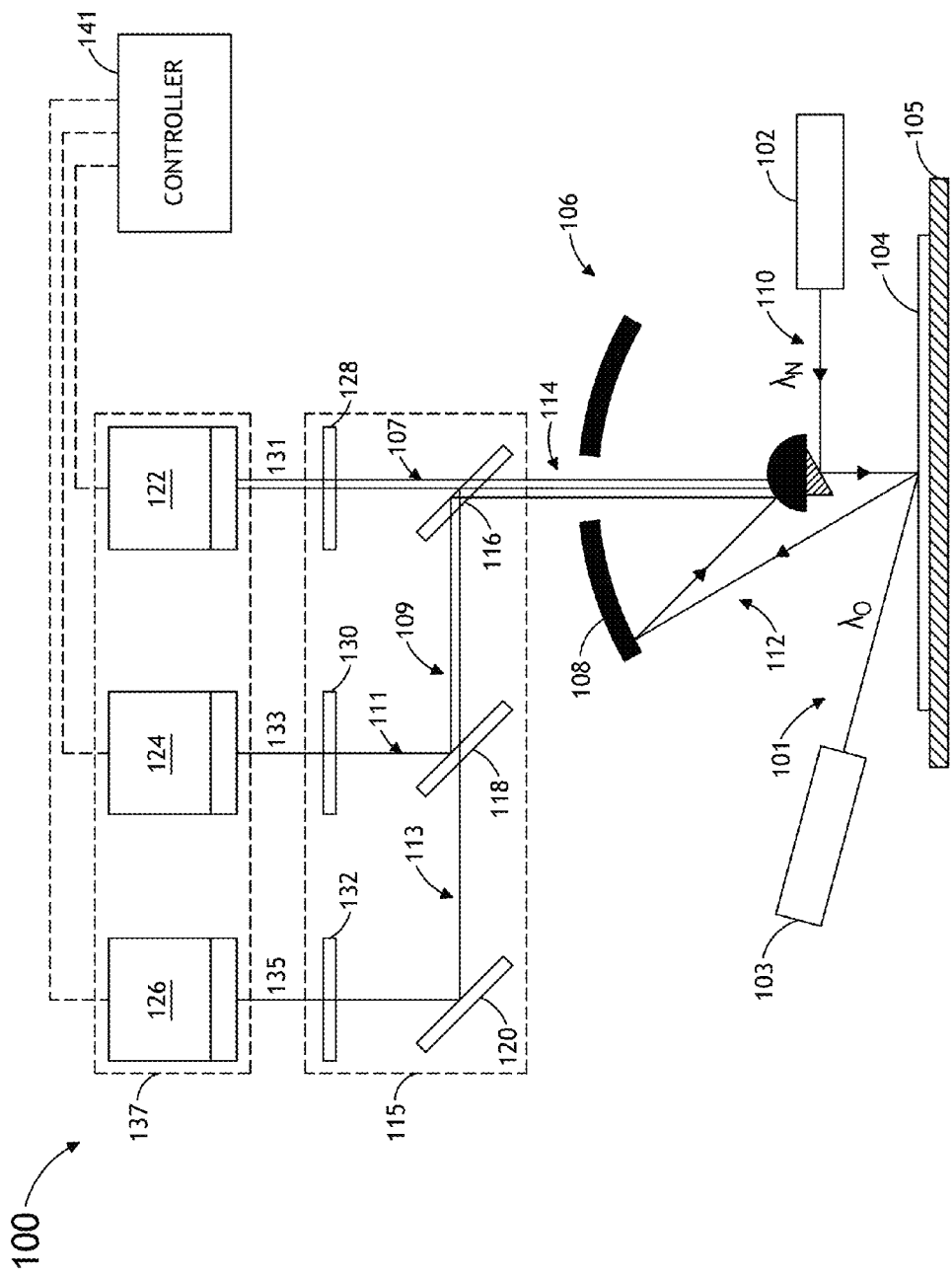
FIG. 1A illustrates a simplified schematic view of a system for defect detection and photoluminescence measurement of a sample, in accordance with one embodiment of the present invention.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention. Reference will now be made in detail to the subject matter disclosed, which is illustrated in the accompanying drawings.

Referring generally to FIGS. 1A through 1J, a system for defect detection and photoluminescence measurement and defect classification on a sample is described, in accordance with the present invention. It is noted herein that certain crystalline defects, such as stacking faults (SFs) and basal plane dislocations (BPDs), present in semiconductor device layers may produce a characteristic, albeit weak, luminescence signature when excited with ultraviolet (UV) radiation (e.g., $\lambda$<385 nm). For example, stacking faults and basal plane defects associated with an epilayer of a wide-bandgap semiconductor power device (e.g., silicon carbide based power device or gallium nitride based power device) may emit photoluminescent light when illuminated with ultraviolet light. In the case of silicon carbide (SiC) based power devices, the ultraviolet light used to stimulate photoluminescence in the associated stacking faults may roughly corresponds to the 4H—SiC bandgap, a SiC polytype commonly used for epilayer growth in the power device industry.

The various embodiments of system 100 (e.g., FIG. 1A) are directed, in part, to an optical architecture and analysis procedure for simultaneously performing photoluminescence (PL) mapping and defect detection in a single platform (e.g., located in the same optical head). Specifically, in some embodiments, the present invention may allow for scattering and photoluminescence defect detection in substrate and epilayer portions of a given sample, such as a wide-bandgap semiconductor based power device. In addition, the various embodiments of the present invention may carry out scattering and photoluminescence defect detection utilizing a spiral scanning inspection configuration (e.g., SURFSCAN system by KLA-TENCOR), which provides a faster inspection process as decelerating, stopping and directional changes are avoided.

The present invention provides for a tunable optical architecture, allowing a given sensor to detect a selected portion (i.e., spectral bin) of a given photoluminescence spectrum. As shown in FIG. 1B, a sample containing multiple types of photoluminescing defects, such as stacking faults or basal plane defects, may generate a robust photoluminescent spectrum 134 (e.g., see peaks 143b-143d of FIG. 1B) when excited with ultraviolet light. It is further noted that each type of stacking fault may generate a characteristic photoluminescent spectral feature, such as a position of the photoluminescent peak. For example, as shown in FIG. 1B, a 4S-type stacking fault may display a peak at approximately 460 nm when excited with a 325 nm laser, a 2S-type stacking fault may display a peak at approximately 500 nm when excited with a 325 nm laser and a bar-type stacking may display a peak at approximately 420 nm when excited with a 325 nm laser. The present invention may independently measure selected spectral bands of the photoluminescence spectrum associated with a given sample and based on those measurements detect and/or classify the constituent photoluminescent defects (e.g., classify types of stacking faults in sample). It is noted herein that while the spectrum depicted in FIG. 1B was acquired with a 325 nm UV laser, the principles displayed in FIG. 1B are also observed in spectrum generated with lasers of wavelengths different than 325 nm, such as, but not limited to, a 355 nm laser.

Figure 1B:
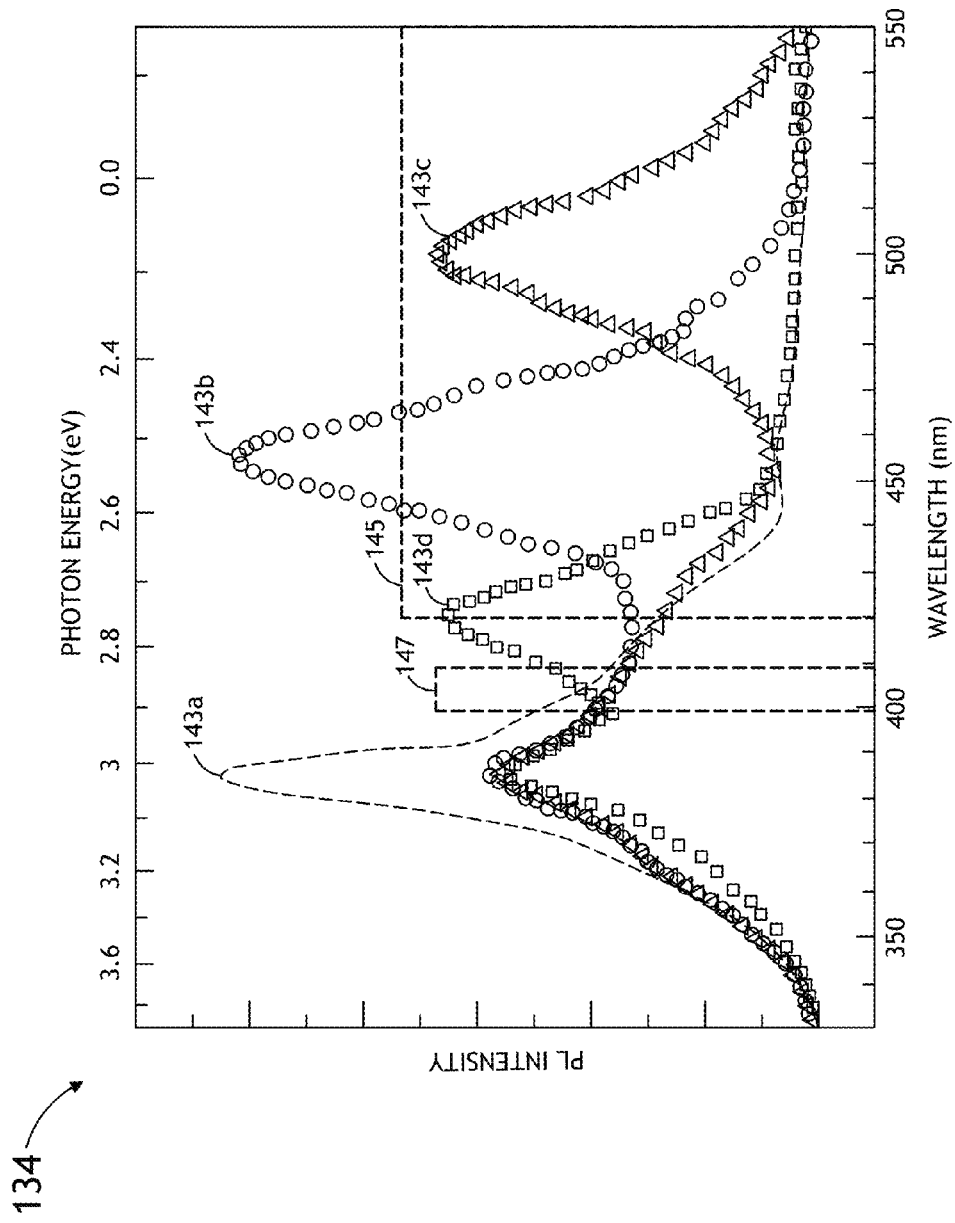
FIG. 1B illustrates a set of spectral integration bins superposed on a photoluminescent spectrum, in accordance with one embodiment of the present invention.

FIG. 1A illustrates a block diagram view of a system 100 for defect detection and photoluminescence measurement of a sample, in accordance with one embodiment of the present invention. In one embodiment, the system 100 includes an oblique-incidence radiation source 103 configured to direct a beam of light 101 (e.g., laser beam) having an oblique-illumination wavelength $\lambda_O$ onto a portion of the sample 104 along a direction oblique to the surface of the sample 104. In another embodiment, the system 100 includes a normal-incidence radiation source 102 configured to direct (via one or more optical elements) a beam of light 110 (e.g., laser beam) having a normal-illumination wavelength $\lambda_N$ onto a portion of the sample 104 along a direction normal to the surface of the sample 104. The oblique-incidence radiation source 103 may emit light at any wavelength or range of wavelengths. Further, the oblique-incidence radiation source 103 may include any radiation source known in the art. For example, the oblique-incidence radiation source 103 may include, but is not limited to, a laser. In one embodiment, the oblique-incidence radiation source 103 may include a visible spectrum laser. For example, the oblique-incidence radiation source 103 may include, but is not limited to, a laser capable of emitting 405 nm light. In an alternative embodiment, the oblique-incidence radiation source 130 may include an ultraviolet spectrum laser.

In one embodiment, the system 100 may detect one or more defects on (or in) the surface of sample 104 by collecting and analyzing the oblique-incidence light that is elastically scattered by the one or more defects. It is noted herein that the inclusion of the oblique-incidence radiation source 103 and the corresponding detection sub-system allows the system 100 to operate in darkfield mode in at least some configurations of the present invention. It is further noted herein that light from the oblique-incidence source 103 aids in differentiation between pit defects and particle defects at the surface of the sample 104 since particle defects display a stronger response to light impinging a substrate at an oblique angle than pit defects. As such, based on the measured response at the wavelength (or wavelength range) corresponding to the oblique-incidence light (e.g., 405 nm), one or more defects at a sample surface may be classified as either a pit defect or particle defect (e.g., classified via controller 141). An inspection system and method suitable for differentiating between pit and particle defects is described in U.S. Pat. No. 6,201,601 to Vaez-Iravani et al., issued Mar. 13, 2011, which is incorporated herein by reference in the entirety.

The normal-incidence radiation source 102 may emit light at any wavelength of range of wavelengths suitable for stimulating one or more photoluminescence defects of the surface of sample 104, such as a stacking fault defects located in the epilayers of the sample 104, to emit photoluminescence light. For example, the normal-incidence radiation 110 may include ultraviolet light. In one embodiment, the wavelength $\lambda_N$ of the normal-incidence radiation 110 is less than the wavelength $\lambda_O$ of the oblique-incidence radiation 101. For instance, the normal-incidence radiation 110 may include ultraviolet light having a wavelength of 355 nm, while the oblique-incidence radiation 101 may have a wavelength of 405 nm. Further, the normal-incidence radiation source 102 may include any radiation source known in the art. For example, the normal-incidence radiation source 102 may include, but is not limited to, a laser. For instance, the normal-incidence radiation source 102 may include, but is not limited to, an ultraviolet laser, such as an ultraviolet continuous wave (CW) laser. For example, the normal-incidence radiation source 102 may include, but is not limited to, an ultraviolet laser capable of emitting 355 nm light. It is noted herein that 355 nm UV light is suitable for stimulating photoluminescence emission in stacking fault defects of a sample. It is further noted that the 355 nm wavelength is not a limitation and is provided merely for illustration. It is recognized herein that different wavelengths of light may be utilized by the normal-incidence light source 102 of the present invention to stimulate photoluminescence emission in different types of photoluminescence defects.

In addition to the photoluminescence stimulating aspects described previously herein, the system 100 may detect one or more defects on the surface of sample 104 by collecting and analyzing the normal-incidence light that is elastically scattered by one or more defects. In this regard, the normal-incidence radiation source 102 and the corresponding detection sub-system allow the system 100 to operate in darkfield mode in at least some applications of the present invention.

It is noted herein that the terms "oblique-illumination wavelength" and "normal-illumination wavelength" are not limiting and are provided for illustration and clarity.

In one embodiment, the system 100 includes a set of collection optics 106 configured to collect radiation from the sample 104. The collection optics 106 may include a collector 108 positioned above the sample 104 and configured to collect light from the sample 104 and direct the collected light to an input of the filter sub-system 115 and on to the various sensors of system 100.

In another embodiment, the radiation 112 emanating from the sample 104 may include radiation elastically scattered by one or more defects of the sample 104 or photoluminescence radiation emitted by one or more photoluminescing defects of the sample 104. For example, the collector 108 is configured to collect the scattered and/or radiated light from the sample 104. For instance, after light 110 from the normal-incidence source 102 and/or light 101 from the oblique-incidence source 103 impinges on the surface of the sample 104 (e.g., epilayers of sample or substrate of sample), the light may be scattered or radiated via photoluminescence by one or more portions of the surface of the sample 104 or defects located at the surface of the sample 104. In turn, the collector 108 may collect the scattered or radiated light and transmit the light to an input of the filter sub-system 115. While the description above describes the invention in the context of the geometry depicted in FIG. 1A, the invention is not limited to such geometry or light collection devices and methods. For instance, it is recognized herein that system 100 may alternatively be configured to collect and measure light reflected from the sample 104.

The collector 108 of the collection optics 106 may include any optical collection device, such as a collector or objective, known in the art. For example, the collector 108 may include, but is not limited to, a reverse Cassegrain-type reflective objective, as shown in FIG. 1A. It is noted herein that the collection optics 106 are not limited to the configuration illustrated in FIG. 1A, which is provided merely for illustrative purposes. It is recognized herein that the collection optics 106 of system 100 may include a number of additional optical elements (e.g., lenses, mirrors, filters, and the like) for collecting illumination being scattered or radiated from the sample 104 and directing that illumination to the filter sub-system 115 and detection sub-system 137 of the present invention. An optical collection sub-system suitable for collecting scattered or photoluminescently radiated light is described in U.S. patent application Ser. No. 12/861,894, filed Aug. 24, 2010, which is incorporated above in the entirety. An additional optical collection sub-system suitable for collecting scattered or photoluminescently radiated light is described in U.S. Pat. No. 7,907,269 to Meeks, issued on Mar. 15, 2011, which is incorporated herein by reference in the entirety.

In another embodiment, the system 100 includes a filter sub-system 115. In one embodiment, the filter sub-system 115 is arranged to receive radiation 114 collected by the set of collection optics 106. For example, radiation 114 from the sample 104, such as scattered light or radiated PL light, may be collected by collector 108 of the collection optics 106 and then transmitted to one or more portions of the filter sub-system 115. In another embodiment, the filter sub-system 115 is configured to separate the radiation 114 from the sample 104 into a first portion of radiation including one or more wavelengths in the visible or near-infrared spectrum associated with the light emitted by the one or more photoluminescing defects of the sample 104, a second portion of radiation including the normal-illumination wavelength $\lambda_N$, and at least a third portion of radiation including the oblique-illumination wavelength $\lambda_O$.

For the purposes of the present disclosure the terms "portion of radiation" and "radiation within a spectral bin" may be used interchangeably. In this regard, the "first portion of radiation including one or more wavelengths in the visible or near-infrared spectrum" may be regarded as the "light within the visible or near-infrared photoluminescence spectral bin." Further, the "second portion of radiation including the normal-illumination wavelength $\lambda_N$" may be regarded as the "light within the second scattering-normal bin" and the "third portion of radiation including the oblique-illumination wavelength $\lambda_O$" may be regarded as the "the light within the third scatter-oblique bin."

In one embodiment, the filter sub-system 115 includes one or more optical elements configured to separate the radiation 114 received from the sample 104 into a first portion 131 of radiation including one or more wavelengths in the visible or near-infrared spectrum associated with the light emitted by the one or more photoluminescing defects of the sample 104, a second portion 133 of radiation including the normal-illumination wavelength $\lambda_N$, and at least a third portion 135 of radiation including the oblique-illumination wavelength $\lambda_O$.

In one embodiment, the system 100 includes a detection sub-system 137 for measuring one or more characteristics of the first portion of radiation 131 transmitted by the filter sub-system 115, one or more characteristics of the second portion of radiation 133 transmitted by the filter sub-system 115 and the third portion of radiation 135 transmitted by the filter sub-system 115. In one embodiment, the detection sub-system 137 includes a first sensor 122 for measuring one or more characteristics of the first portion of radiation 131 transmitted by the filter sub-system, a second sensor 124 for measuring one or more characteristics of the second portion 133 of radiation transmitted by the filter sub-system 115 and at least a third sensor 126 for measuring one or more characteristics of the third portion 135 of radiation transmitted by the filter sub-system 115.

In one embodiment, the first optical element 116 may separate a first spectral range of radiation 107 including the first portion of radiation from the radiation 114 received from the sample and direct the first spectral range of radiation 107 toward the first sensor 122 of the detection sub-system 137.

In another embodiment, a second optical element 118 may receive radiation 109 from the first optical element 116 that is not included in the first spectral range of radiation 107. In another embodiment, the second optical element 118 may separate a second spectral range of radiation 111, including the second portion of radiation from the radiation 109 received from the first optical element and direct the second spectral range of radiation 111 toward the second sensor 124 of the detection sub-system 137.

In another embodiment, a third optical element 120 may receive radiation 113 from the second optical element 118 not included in the first spectral range of radiation 107 or the second spectral range of radiation 111. In another embodiment, the third optical element 120 may direct at least a portion of the third spectral range of radiation 113 including the third portion of radiation toward the third sensor 126 of the detection sub-system 137.

It is noted that the optical elements of the filter sub-system 115 may include any optical elements known in the art suitable for separating the light 114 received from the sample into the first, second and third spectral ranges of radiation, as shown in FIG. 1A.

In one embodiment, the first optical element 116 may include a first dichroic beam splitter, such as a long wave pass (LWP), suitable for separating a first spectral range of radiation 107 including the first portion of radiation from the radiation 114 received from the sample and directing the first spectral range of radiation 107 toward the first sensor 122. In another embodiment, the second optical element 118 may include a second dichroic beam splitter (e.g., LWP filter) suitable for receiving radiation 109 from the first dichroic beam splitter 116, separating a second spectral range of radiation 111 including the second portion of radiation from the radiation 109 received from the first dichroic beam splitter and directing the second spectral range of radiation 111 toward the second sensor 124.

In another embodiment, the third optical element 120 may include a mirror 120 for receiving radiation 113 from the second dichroic beam splitter and directing at least a portion of a third spectral range of radiation 113 including the third portion of radiation toward the third sensor 126.

In an alternative embodiment, the third optical element 120 may be configured to at least separate a portion of a third spectral range of radiation 113 including the third portion of radiation from the radiation received from the second optical element 118 and direct the third spectral range of radiation 113 toward the third sensor 126, while transmitting radiation not included in the first spectral range of radiation 107, the second spectral range of radiation 109 or the third spectral range of radiation 113 to one or more additional optical devices (not shown in FIG. 1A) located downstream from the optical element 120. In this example, the mirror 120 shown in FIG. 1A may be replaced with a dichroic beam splitter (e.g., LWP filter), which serves to provide an additional access port to the light. For example, the light passing through the dichroic beam splitter in this embodiment may be couple to an external detector via an optical-fiber. In this regard, the system 100 may further analyze this portion of radiation. For instance, although not shown, the system 100 may include a spectrometer arranged to analyze light passing through the optical element 120. A spectrometer system suitable for analyzing light not diverted to sensors 122, 124 or 126 is described generally in U.S. application Ser. No. 12/861,894, which is incorporated above by reference in the entirety.

In one embodiment, the filter sub-system 115 may be configured to selectively filter light 114 received from the sample 104 such that the sensors 122, 124 and 126 of the detection sub-system 137 each receive a pre-selected band of light.

In another embodiment, the filter sub-system includes a set of narrow band filters in order to allow the system 100 to selectively measure the various radiation bands of interest, as shown in FIG. 1A. In one embodiment, the filter sub-system 115 of system 100 includes a first narrow band filter 128. For example, the first narrow band pass filter 128 may be positioned between the first sensor 122 and the first optical element 116. In this regard, the first narrow band pass filter 128 may receive the first spectral range of radiation 107 from the optical element 116 and transmit the first portion of radiation 131 to the first sensor 122, while blocking radiation not included in the first portion of radiation.

In another embodiment, the filter sub-system 115 of system 100 includes a second narrow band pass filter 130. For example, the narrow band pass filter 130 may be positioned between the second sensor 124 and the second optical element 118. In this regard, the second narrow band pass filter 130 may receive the second spectral range of radiation 111 and transmit the second portion of radiation 133 to the second sensor 124, while blocking radiation not included in the second portion of radiation 133.

In another embodiment, the filter sub-system 115 of system 100 includes a third narrow band pass filter 132. For example, the narrow band pass filter 132 may be positioned between the third sensor 126 and the third optical element 120. In this regard, the third narrow band pass filter 132 may receive the third spectral range of radiation 113 and transmit the third portion of radiation 135 to the third sensor 126, while blocking radiation not included in the third portion of radiation 135.

While system 100 has been described in the context of using narrow band filters and LWP filters to direct the various bands of light to the corresponding sensors, the present invention is not limited to this optical architecture. Rather, the optical configuration depicted with respect to system 100 is provided merely for illustration and is not limiting. It is anticipated that a variety of analogous optical configurations may be implemented in order to separate radiation 114 from the sample 104 into the desired spectral bands of the present invention. For example, the system 100 may include an optical configuration equipped with one or more spectrometers. By way of another example, the system 100 may include an optical configuration equipped with one or more diffractive elements (e.g., diffraction grating) optically coupled to a photodetector. By way of another example, the system 100 may include an optical configuration equipped with one or more dispersive elements (e.g., prism) optically coupled to a photodetector.

In one embodiment, the filter sub-system 115 and the sensor 122 may be arranged such that the first sensor 122 receives light corresponding with visible PL light or near-IR light radiated from one or more PL defects of the sample 104. In one embodiment, the normal-incidence source 102 may illuminate one or more portions of the sample 104 with ultraviolet light, such as laser light having a wavelength of approximately 355 nm. In response, PL defects present in the epilayers of the sample may absorb the UV light and then radiate light in the visible and/or near-IR spectrum. Then, the first narrow bandpass filter 128 may transmit light of a selected band, such as light between 417 and 900 nm, to the first sensor 122, allowing the system 100 to detect stacking faults in the visible and/or near IR spectrum. As described further herein, the spectral location and width of the selected band may be a function of anticipated PL features present in a given sample 104, allowing the system 100 to be tuned to a particular PL detection scenario.

In another embodiment, the filter sub-system 115 and the sensor 124 may be arranged such that the second sensor 124 receives light including normal-incidence wavelength light $\lambda_N$ scattered by defects and/or the sample surface. In one embodiment, the normal-incidence source 102 may illuminate one or more portions of the sample 104 with normal-incidence light 110 of wavelength $\lambda_N$ (e.g., ultraviolet light, such as 355 nm light). In response, one or more defects or portions of the sample 104 surface may scatter or reflect the $\lambda_N$ light. Then, the second narrow bandpass filter 130 may transmit light of a selected band, such as a wavelength band including light emitted by the $\lambda_N$-source, to the second sensor 124. For example, in the case where the normal-incidence source 102 is a UV source, emitting light at 355 nm, the second narrow bandpass filter 130 may be configured to transmit light in the range 350-360 nm.

In another embodiment, the filter sub-system 115 and the third sensor 126 may be arranged such that the third sensor 126 receives light including oblique-incidence wavelength light $\lambda_O$ scattered by defects and/or the sample 104 surface. In one embodiment, the oblique-incidence source 103 may illuminate one or more portions of the sample 104 with oblique-incidence light 101 of wavelength $\lambda_O$ (e.g., 405 nm light). In response, one or more defects or portions of the sample 104 surface may scatter or reflect the $\lambda_O$ light. Then, the third narrow bandpass filter 132 may transmit light of a selected band, such as a wavelength band including light emitted by the $\lambda_O$-source, to the third sensor 126. For example, in the case where the oblique-incidence source 103 emits light at 405 nm, the third narrow bandpass filter 132 may be configured to transmit light in the range 400-410 nm, allowing the system 100 to detect stacking faults in the UV spectrum. By way of another example, in the case where the oblique-incidence source 103 emits light at 405 nm, the third narrow bandpass filter 132 may be configured to transmit light in the range 370-410 nm, allowing the system 100 to detect stacking faults and basal plane dislocation defects in the near-UV (NUV) spectrum.

It is noted herein that the implementation of the filter sub-system 115 and detection sub-system 137 described above allows the system 100 to isolate various signal contributions from the illuminated sample 104. In this regard, it is possible to simultaneously measure the scattering of oblique-incidence illumination, the scattering of normal-incidence illumination and radiated PL light, stimulated by a UV source in a manner allowing for the isolated measurement of each. In addition, the configuration described above aids in avoiding cross-talk for the scattered oblique-incidence light and the scattered normal-incidence light (i.e., the coupling of undesired bands into low levels of scattered light).

It is noted herein that the sensors 122, 124 and 126 (and the sensors of embodiments described further herein) may include any type of light sensor architecture known in the art. For example, the sensors of system 100 may include, but are not limited to, photomultiplier tubes (PMTs). In an alternative embodiment, the sensors of the system 100 may include, but are not limited to photodiodes (e.g., avalanche photodiodes).

Figure 1C:
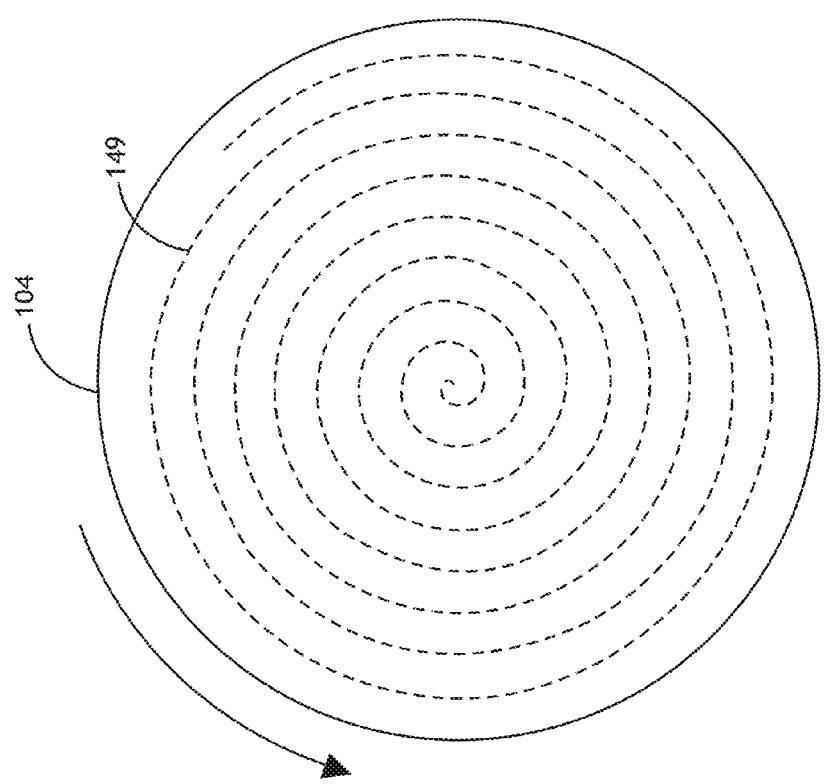
FIG. 1C illustrates a conceptual view of an inspection path of a spiral scan inspection system, in accordance with one embodiment of the present invention.
Figure 1D:
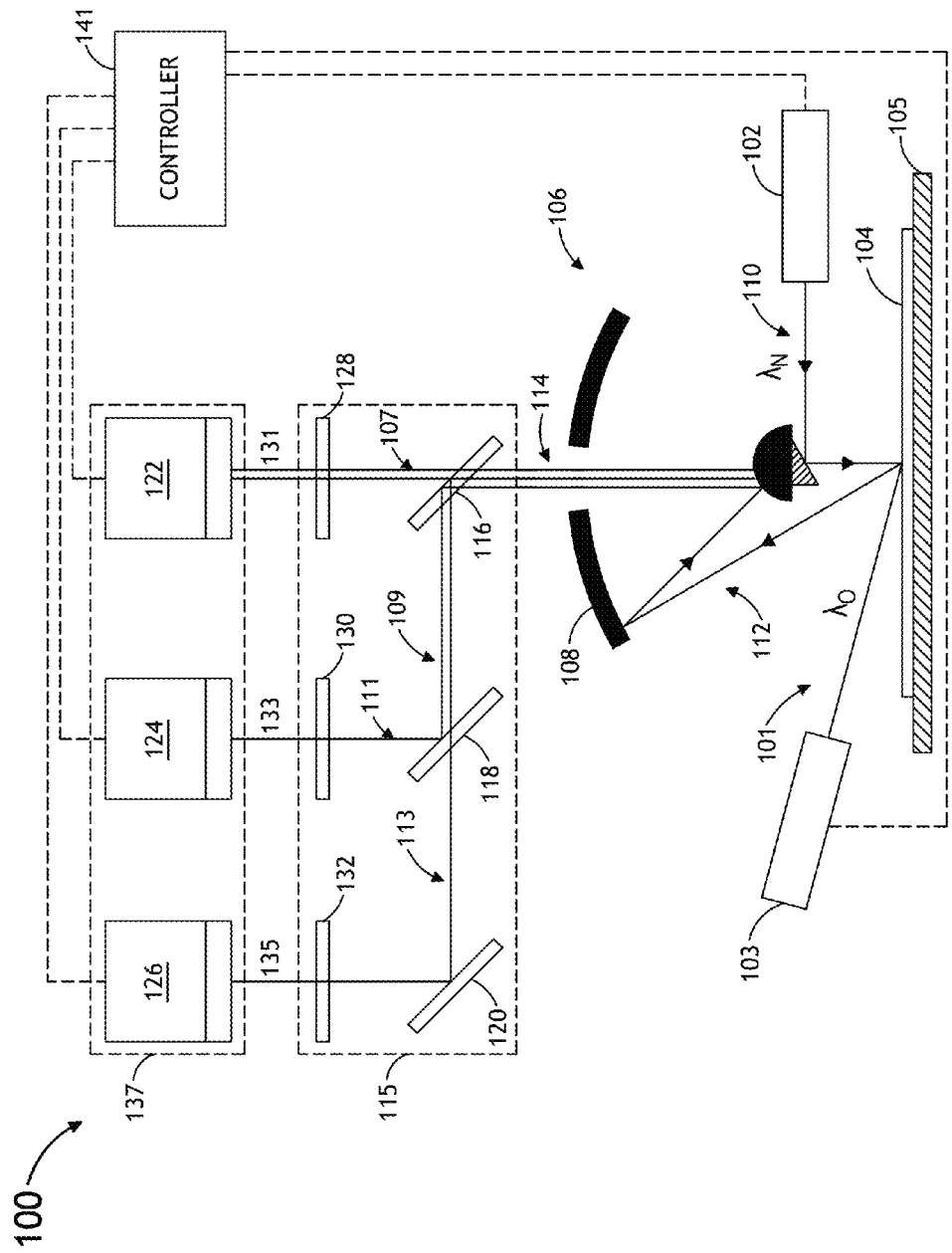
FIG. 1D illustrates a simplified schematic view of a system for defect detection and photoluminescence measurement of a sample, in accordance with one embodiment of the present invention.

In one embodiment, the system 100 includes a controller 141 communicatively coupled to one or more portions of the detection sub-system 137, as show in FIGS. 1A and 1D. In one embodiment, the controller 141 is communicatively coupled to the first sensor 122, the second sensor 124 and the third sensor 126 of the detection sub-system 137. In this regard, the controller 141 (e.g., one or more processors of the controller 141) may receive measurement results from the first sensors 122, the second sensor 124 and the third sensor 126.

In one embodiment, the controller 141 may receive a signal indicative of one or more characteristics (e.g., signal intensity) of the first portion of radiation, corresponding to light falling within the defined visible or near-infrared spectral bin (e.g., 417-900 nm), which includes, at least in part, the visible and/or near-infrared light emitted by the one or more photoluminescing defects of the sample 104. In another embodiment, the controller 141 may receive a signal indicative of one or more characteristics (e.g., signal intensity) of the second portion of radiation, corresponding to the light falling within the defined scattering-normal spectral bin (e.g., 350-360 nm), which includes a wavelength range including the normal-incidence wavelength $\lambda_N$ (e.g., 355 nm). In another embodiment, the controller 141 may receive a signal indicative of one or more characteristics (e.g., signal intensity) of the third portion of radiation, corresponding to the light falling with the defined scattering-oblique spectral bin (e.g., 400-410 nm), which includes a wavelength range including the oblique-incidence wavelength $\lambda_O$ (e.g., 405 nm).

In one embodiment, the controller 141 may detect one or more scattering defects based on the light measured by at least one of the second sensor 124 and the third sensor 126. In one embodiment, the controller 141 may analyze the one or more signals of the second sensor 124 in order to identify a defect, such as a particle, scattering $\lambda_N$ light (e.g., 355 nm). In another embodiment, although not shown, the system 100 may be configured to utilize the normal-incident channel (i.e., source 102 and sensor 124 in UV spectrum) in reflection mode (i.e., brightfield channel) in order to measure specular reflectivity and one or more slope channels due to the opaque nature of various wide bandgap semiconductor materials (e.g., SiC and GaN) to UV light, yielding high image quality. In another embodiment, although not shown, the system 100 may be configured to utilize reflected light from the oblique-incident channel (e.g., 405 nm light) to yield multi-channel signals such as, but not limited to, specular reflectivity, slope channel data and phase channel data.

In one embodiment, the controller 141 may analyze the one or more signals of the third sensor 126 in order to identify a defect, such as a particle, which scatters light having a wavelength of $\lambda_O$ (e.g., 405 nm). In another embodiment, system 100 may utilize oblique reflected light of wavelength $\lambda_O$ to yield multichannel signals, such as, but not limited to, specular reflectivity, slope and phase channels.

In another embodiment, the system 100 may include one or more confocal apertures (not shown) in order to aid in separating backside scatter from frontside scatter in cases where the illumination wavelength (e.g., 405 nm) is transparent to the given wide bandgap material (e.g., SiC) of the sample 104. The application of one or more confocal apertures is described generally in U.S. Pat. No. 7,907,269 to Meeks, filed on Jun. 24, 2010, which is incorporated herein by reference in the entirety.

In another embodiment, the controller 141 may detect one or more photoluminescence defects based on at least one of the one or more characteristics, such as one or more signal characteristics (e.g., signal intensity), measured by the first sensor, the one or more characteristics measured by the second sensor and the one or more characteristics measured by the third sensor. In another embodiment, the controller 141 may detect one or more photoluminescence defects by comparing the one or more characteristics from at least one of the first sensor 122, the second sensor 124 and the third sensor 126 in an area of the sample 104 absent of photoluminescing defects to a signal from at least one of the first sensor 122, the second sensor 124 and the third sensor 126 acquired from a measured region of the sample 104. In one embodiment, in obtaining a measurement of signal intensity of an area void of photoluminescence defects, one or more of the sensors 122-126 may acquire detection data from areas known to be void of photoluminescence defects. Curve 143a is a set of photoluminescence intensity versus wavelength curves of a region of a sample void of photoluminescence defects. It is noted herein that this photoluminescence-defect-free curve 143a may then be compared to data acquired from additional regions of the sample 104 in order to identify one or more photoluminescence defects.

In another embodiment, the controller 141 may map the detected one or more photoluminescence defects based on at least one of the one or more characteristics measured by the first sensor, the one or more characteristics measured by the second sensor and the one or more characteristics measured by the third sensor along with the known position of the detected one or more photoluminescence defects. In this regard, a two-dimensional map may be generated by the detector, whereby the spectral signature measured by each detector is plotted at a given measurement position. In this manner, a topographical map displaying the mapping of multiple spectral bands may be displayed. In alternative embodiment, the controller 141 may selectively display only a portion of the multiple spectral bands. In this regard, the controller 141 may display a map of features measured in a single spectral band or display a map of features measured in two or more spectral bands.

In another embodiment, the controller 141 may classify the detected one or more photoluminescence defects based on at least one of the one or more characteristics, such as spectral characteristics (e.g., spectrum, intensity, spectral position of one or more peaks) measured by the first sensor, the one or more characteristics measured by the second sensor and the one or more characteristics measured by the third sensor. It is noted herein that a particular type of photoluminescence defect (or defects) will display a characteristic spectrum, as previously described and shown by curves 143b-143d of FIG. 1B. By measuring the intensity of a particular spectral bin, such as spectral bin 145 and/or spectral bin 147 shown in FIG. 1B, the controller 141 may determine the type of photoluminescence defect being measured. For example, the controller 141 may compare the measured and detected results previously described herein to a look-up table in order to identify the type of one or more detected photoluminescence defects. For instance, a look-up table containing information that correlates various types of photoluminescence defects, such as stacking fault defects (e.g., bar-shaped stacking faults, 2SSF stacking faults, 4SSF stacking faults and the like), to a corresponding photoluminescence spectrum may be built up by the system 100 (or an additional system) and stored in memory. Photoluminescence spectra associated with particular stacking faults is generally described in Feng et al., "Characterization of Stacking Faults in 4H—SiC Epilayers by Room-Temperature Microphotoluminescence Mapping," *Applied Physics Letters, Vol.* 92, Issue 22 (2008), which is incorporated herein by reference in the entirety. It is noted herein that effective classification is achieved in settings with additional sensors, whereby each of the sensors are matched to a given spectral bin corresponding to a known spectral signature for a given stacking fault time. This approach is discussed in greater detail further herein.

Figure 1E:
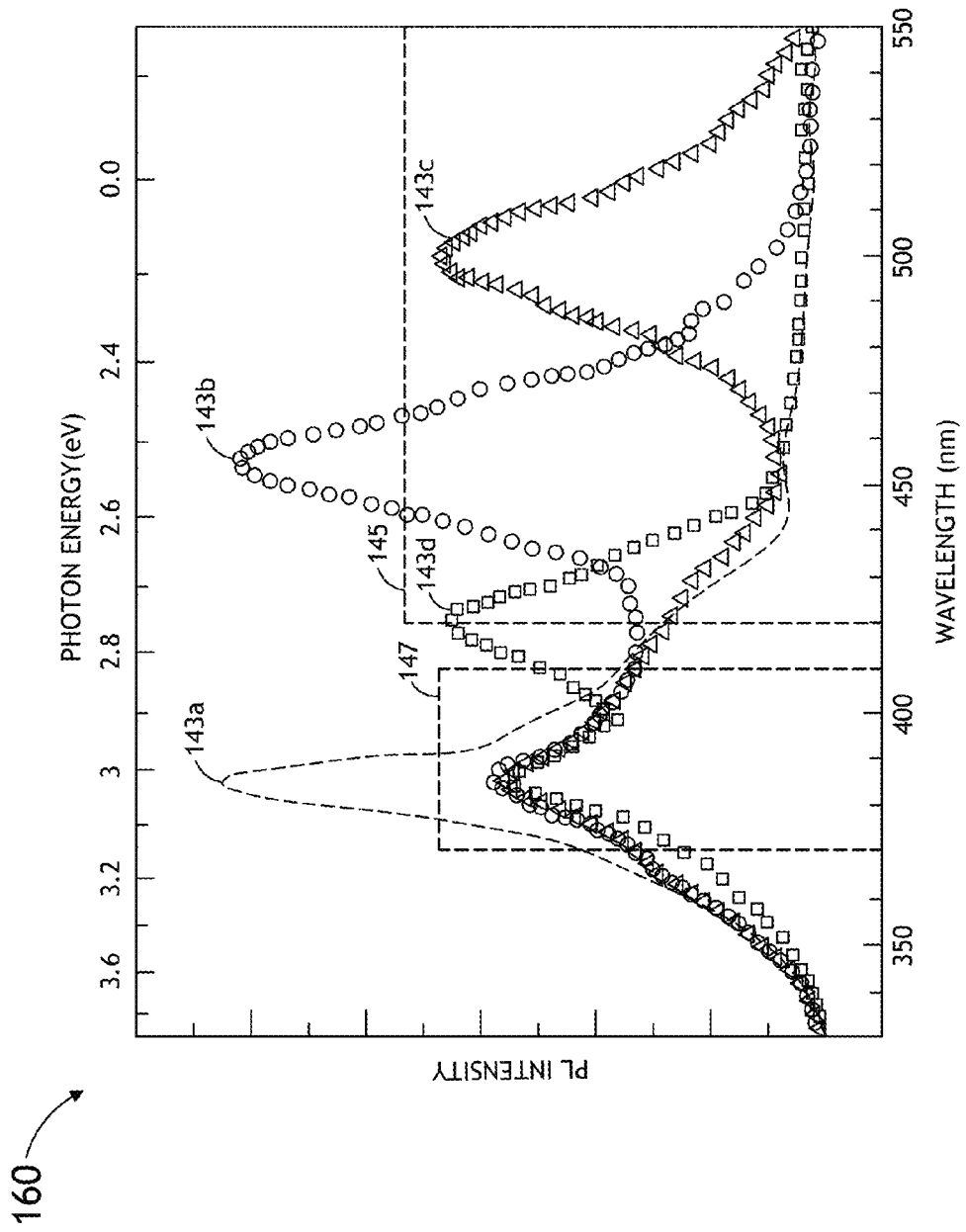
FIG. 1E illustrates a set of spectral integration bins superposed on a photoluminescent spectrum, in accordance with one embodiment of the present invention.

In one embodiment, the spectral bin 145 may represent the UV-to-Visible photoluminescence integration band that is produced by stimulating photoluminescence with a 355 nm laser and detecting photoluminescence light using a 420-700 nm spectral band, effectuated with the filter sub-system 115 and detection sub-system 137 as described previously herein. In another embodiment, as shown in FIG. 1B, the spectral bin 147 may represent the UV-to-UV photoluminescence integration band that is produced by stimulating photoluminescence with a 355 nm laser and detecting photoluminescence light using a 400-410 nm spectral band, effectuated with the filter sub-system 115 and detection sub-system 137 as described previously herein. In another embodiment, as shown in FIG. 1E, the spectral bin 147 may represent a UV-to-NUV photoluminescence integration band that is produced by stimulating photoluminescence with a 355 nm laser and detecting photoluminescence light using a broader band, such as, but not limited to, a 370-410 nm spectral band, effectuated with the filter sub-system 115 and detection sub-system 137 as described previously herein. In additional embodiments, it is noted that the spectral bin 147 may correspond to spectral ranges such as, but not limited to, 370-400 nm for the purposes of detecting NUV emitting defects. It is noted herein that the spectral binning configuration of FIG. 1E is suitable for detecting both stacking faults and basal plane dislocations.

It is noted herein that the visible/NIR detection using spectral bin 145 may correspond to a 'positive' contrast, or 'bright' contrast, detection process, whereby the intensities of the characteristic peaks in the photoluminescence spectrum are larger than the background intensity corresponding with the photoluminescence-defect-free curve 143a. In contrast, the NUV detection using spectral bin 147 (e.g., corresponding with a band of 370-410 nm and the like) may correspond with a 'negative' contrast, or 'dark' contrast, detection process, whereby the intensities of the characteristic peaks in the photoluminescence spectrum are smaller than the background intensity corresponding with the photoluminescence-defect-free curve 143a.

Figure 1F:
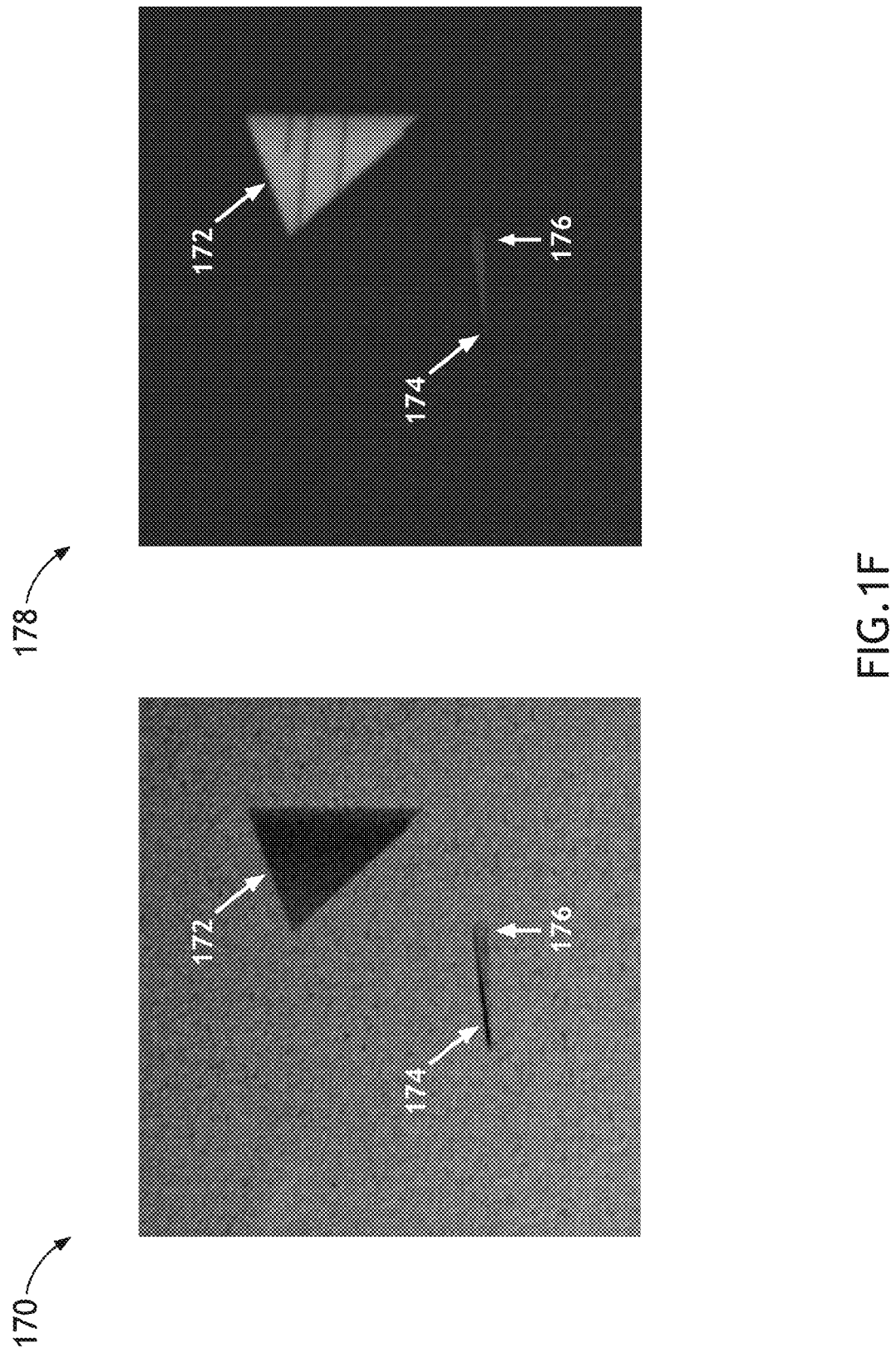
FIG. 1F illustrates a imagery data of a stacking fault defect and a basal plane dislocation acquired in dark contrast mode and bright contrast mode, in accordance with an embodiment of the present invention.

FIG. 1F illustrates a pair of photoluminescence inspection images depicting imagery data obtained utilizing the NUV-based dark contrast detection scheme and the visible-based bright contrast detection scheme, in accordance with one or more embodiments of the present invention. Image 170 depicts imagery data obtained utilizing a spectral bin corresponding to the NUV band described above (e.g., 370-410 nm). As shown in image 170, the stacking fault 172 and basal plane dislocation 174 both display a high level of negative contrast. The stacking fault portion 176 of the split basal plane dislocation, however, displays fainter negative contrast. Image 178 depicts imagery data obtained utilizing a spectral bin corresponding to the visible band described above (e.g., 420-700 nm). As shown in image 178, the stacking fault 172 and the stacking fault portion 176 of the split basal plane dislocation both display relatively strong positive contrast. However, the basal plane dislocation 174 displays no measurable bright contrast in image 178. It is noted herein that the basal plane dislocation 174 is also known to be faintly bright in the NIR band, such as 750-900 nm.

In an alternative embodiment, as illustrated in FIG. 1D, the controller 141 is configured to selectably deactivate the oblique-incidence radiation source 103. In one embodiment, the second sensor 124, which may detect radiation in a range at least including light of $\lambda_O$, may be utilized to detect photoluminescence radiation emitted by one or more photoluminescent defects. In a further embodiment, the controller 141 may deactivate the oblique-incidence radiation source 103 prior to the photoluminescence measurement by the second sensor 124. For example, in the case where $\lambda_O$=405 nm and the sensor 124 is configured to detect radiation in the band 400-410 nm, the controller 141 may deactivate the oblique-incidence radiation source 103 in order to sample photoluminescence light within the 400-410 nm band, which was generated via the stimulation by the 355 nm ultraviolet radiation source 102. It is recognized herein that this detection scenario (i.e., detecting defect scattered $\lambda_O$ radiation and detecting photoluminescence radiation in the same range) may be carried out utilizing two inspection passes of the wafer.

In one embodiment, the controller 141 includes one or more processors (not shown) and a non-transitory storage medium (i.e., memory medium). In this regard, the storage medium of the controller 141 (or any other storage medium) contains program instructions configured to cause the one or more processors of controller 141 to carry out any of the various steps described through the present disclosure. For the purposes of the present disclosure the term "processor" may be broadly defined to encompass any processor or logic element(s) having processing capabilities, which execute instructions from a memory medium. In this sense, the one or more processors of controller 141 may include any microprocessor-type device configured to execute software algorithms and/or instructions. In one embodiment, the one or more processors may consist of a desktop computer or other computer system (e.g., networked computer) configured to execute a program configured to execute the computational/data processing steps described throughout the present disclosure. It should be recognized that the steps described throughout the present disclosure may be carried out by a single computer system, multiple computer systems, or a multi-core processor. Moreover, different subsystems of the system 100, such as a display device or a user interface device (not shown), may include a processor or logic elements suitable for carrying out at least a portion of the steps described above. Therefore, the above description should not be interpreted as a limitation on the present invention, but rather merely an illustration.

In one embodiment, the system 100 includes a sample stage assembly 105 configured to secure the sample 104 and selectively actuate the sample 104 in order to perform a scanning process with at least the oblique-incidence radiation source 103 and the normal-incidence radiation source 102. In this regard, the sample stage 105 and/or the optical head containing the oblique-incidence radiation source 103 and the normal-incidence radiation source 102 may be selectively actuated, thereby scanning the sample 104 relative to the incident light beams 101 and 110.

In one embodiment, the sample stage assembly 105 of system 100 includes a rotational sample stage assembly configured to secure the sample 104 and selectively rotate the sample 104. In one embodiment, the rotational sample stage assembly includes a sample chuck (not shown) for securing the sample 104. For example, the sample chuck may include, but is not limited to, a vacuum chuck. In another embodiment, the rotational sample stage assembly includes a sample spindle (not shown) configured to selectively rotate the sample 104. For example, the sample spindle may rotate the sample 104 at a selected rotational speed about an axis perpendicular to the surface of the sample 104. In another embodiment, the spindle may selectively rotate (or stop rotation) of the sample in response to an associated controller or control system (e.g., controller 141).

In one embodiment, a rotational sample stage of system 100 is configured to carry out a spiral scanning process. In one embodiment a rotational sample stage of system 100 may rotate the sample 104 at a selected rotational speed, while an optical head including the oblique-incidence source 103 and the normal incidence source 102 is translated along a selected linear direction (e.g., along a radial line of the sample 104). For example, the optical head may be coupled to a linear stage suitable for translating the optical head along a selected linear direction. The combined motion of the rotation of the sample 104 and the linear motion of the oblique-incidence source 103 and the normal incidence source 102 generates a spiral scanning pattern 149, as shown in FIG. 1C. In this regard, the sample 104, such as a SiC wafer, may be rapidly rotated (e.g., 5000 RPM) under the optical head (including source 102 and source 103) and moved slowly along one radius of the sample 104 with a selected track pitch (e.g., 4 µm). For instance, the optical head may be moved along a radial direction from the edge of the sample to the center of the sample.

It is noted herein that the spiral scanning technique provides for a relatively fast scanning process as no time is required for decelerating, accelerating, stopping or changing directions, which is required in most X-Y scanning architectures (e.g., scanning, swathing, or move-acquire-measure configurations). A spiral scanning architecture suitable for implementing the spiral scanning procedure described herein is described generally in U.S. Pat. No. 6,201,601 to Vaez-Iravani et al., filed on Sep. 19, 1997, which is incorporated herein in the entirety.

In an alternative embodiment, the sample stage assembly 105 of system 100 includes a linear stage assembly (not shown) configured to secure the sample 104 and selectively translate the sample 104 along at least a first direction (e.g., X-direction) and a second direction (e.g., Y-direction) perpendicular to the first direction in order to perform an X-Y scanning process with at least the oblique-incidence radiation source 103 and the normal-incidence radiation source 102.

Figure 1G:
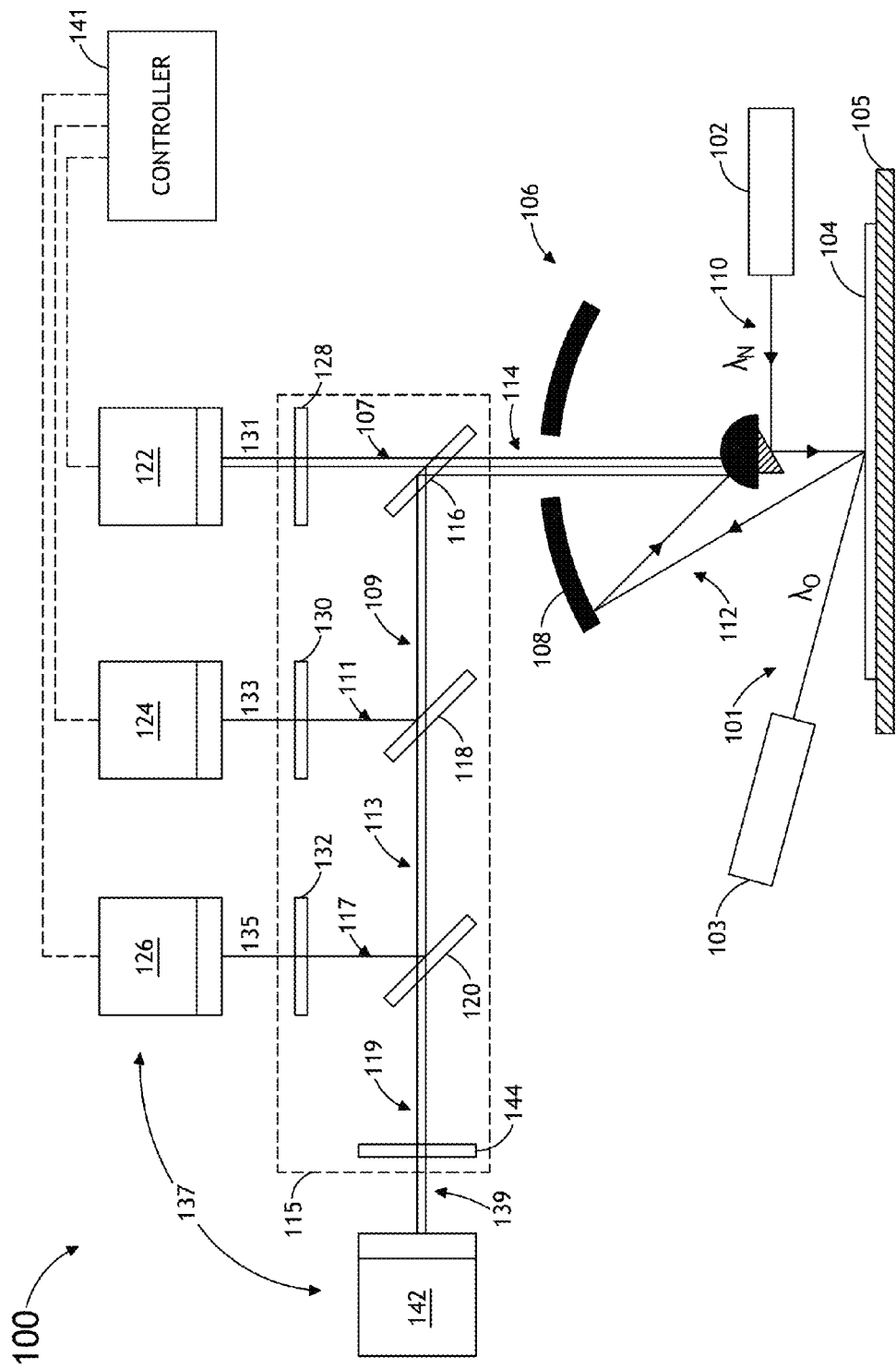
FIG. 1G illustrates a simplified schematic view of a system for defect detection and photoluminescence measurement of a sample, in accordance with one embodiment of the present invention.

FIG. 1G illustrates a block diagram view of system 100, in accordance with an alternative embodiment of the present invention. It is noted herein that the embodiments and examples described previously herein with respect to system 100 should be interpreted to extend to the embodiments of system 100 depicted in FIG. 1G unless otherwise noted.

It is further noted herein that the embodiment depicted in FIG. 1E serves to provide an additional ultraviolet detection band, allowing system 100 to simultaneously detect defect scattered light at $\lambda_O$ (e.g., light generated by oblique-incidence light source 103) as well as ultraviolet photoluminescent light generated by the stimulation of one or more photoluminescent defects by the normal-incidence light source 102.

In one embodiment, the detection sub-system 137 includes a fourth sensor 142 for measuring one or more characteristics of a fourth portion 139 of radiation transmitted by the filter sub-system 115. In one embodiment, the fourth portion of radiation corresponds to ultraviolet radiation having a wavelength less than the smallest wavelength of the third portion of radiation 135. For example, in the case where the third sensor 126 measures oblique scattered light across a band of 400-410 nm (e.g., $\lambda_O$=405 nm), the fourth sensor 142 may be configured to measure radiation below 400 nm. For instance, the fourth sensor 142 may sample radiation in the band 370-400 nm, which may correspond to at least a portion of the ultraviolet band corresponding to ultraviolet light generated by the ultraviolet excitation of one or more photoluminescent defects, which can be observed in the photoluminescence spectral data in FIG. 1B.

In another embodiment, the third optical element 120 of the filter sub-system 115 is configured to receive radiation from the second optical element 118 not included in the first spectral range of radiation 107 or the second spectral range of radiation 111. Further, the third optical element 120 is configured to at least separate a portion of a third spectral range of radiation 117 including the third portion of radiation 135 from the radiation received from the second optical element 118 and direct the third spectral range of radiation 117 toward the third sensor 126. In addition, the third optical element 120 is further configured to transmit radiation not included in the first spectral range of radiation 107, the second spectral range of radiation 111 or the third spectral range of radiation 117 toward the fourth sensor 142 in a fourth spectral range of radiation 119 including a fourth portion of radiation 139. In another embodiment, the third optical element 120 of the filter sub-system 115 may include, but is not limited to, a dichroic optical element (e.g., LWP filter).

In another embodiment, the filter sub-system 115 may include a fourth narrow pass filter 144. In one embodiment, the fourth narrow pass filter 144 is positioned between the fourth sensor 142 and the third optical element 120 and is configured to receive the fourth spectral range of radiation 119 and transmit the fourth portion 139 of radiation, such as ultraviolet photoluminescent light (e.g., 370-400 nm) to the fourth sensor 142 and block radiation not included in the fourth portion of radiation.

Figure 1H:
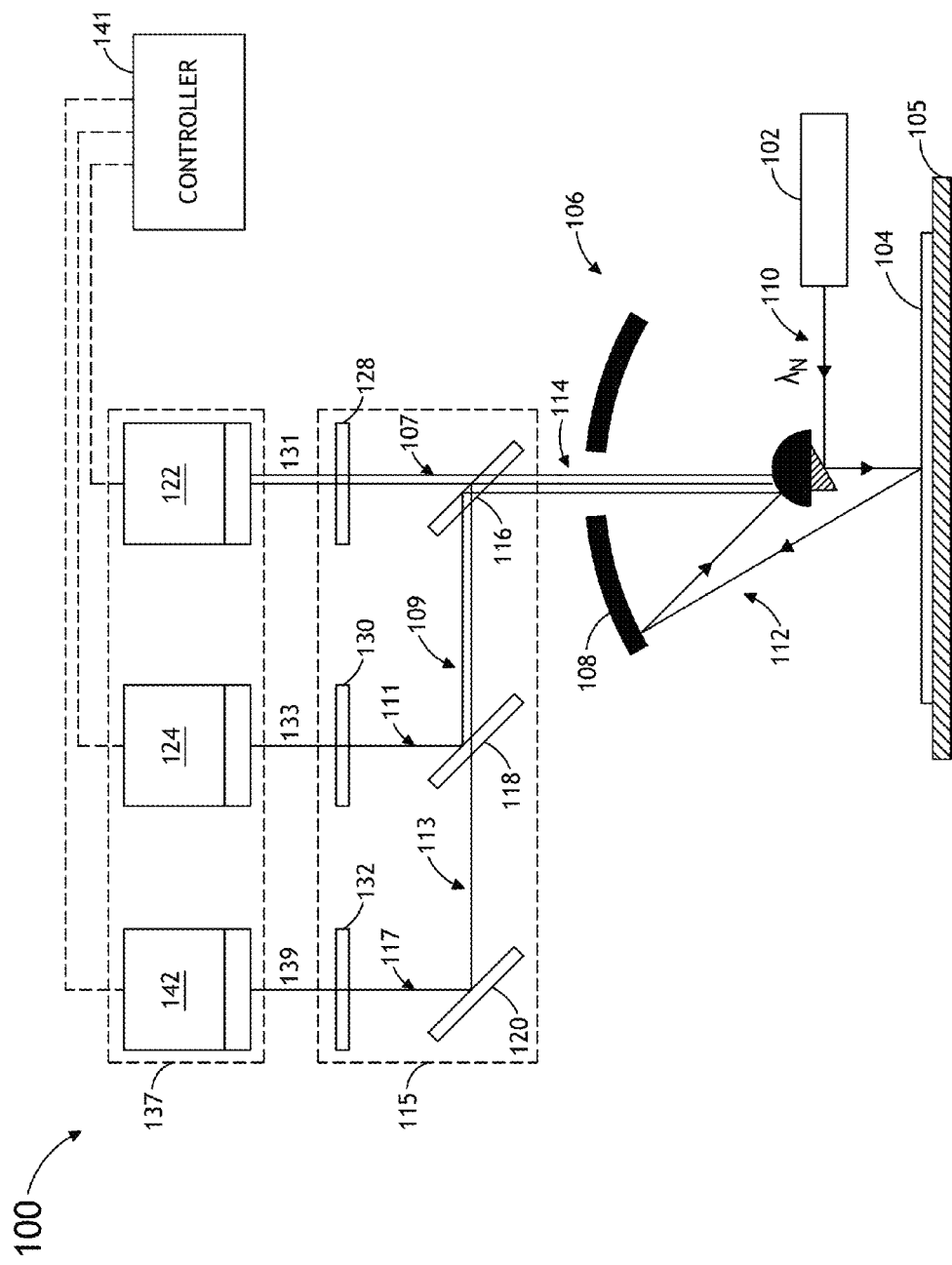
FIG. 1H illustrates a simplified schematic view of a system for defect detection and photoluminescence measurement of a sample, in accordance with one embodiment of the present invention.

FIG. 1H illustrates a block diagram view of system 100, in accordance with an alternative embodiment of the present invention. It is noted herein that the embodiments and examples described previously herein with respect to system 100 should be interpreted to extend to the embodiments of system 100 depicted in FIG. 1H unless otherwise noted.

It is further noted herein that the embodiment depicted in FIG. 1H serves to provide a detection scenario without the oblique-incidence source described previously herein. In this embodiment, system 100 detects scattered light only via the second sensor 124, which is configured to measure one or more characteristics of the second portion 133 of radiation (e.g., 350-360 nm) transmitted by the filter sub-system 115. It is further noted that in the context of this embodiment the third sensor of this embodiment 142 is substantially similar to the fourth sensor 142 of the embodiment described previously herein in FIG. 1G. In this regard, the third sensor 142 of FIG. 1H may measure one or more characteristics of a third portion 139 of radiation transmitted by the filter sub-system 115. In one embodiment, the third portion 139 of radiation corresponds to ultraviolet radiation having a wavelength larger than the largest wavelength of the second portion of radiation 133. For example, in the case where the second sensor 124 measures normal scattered light across a band of 350-360 nm (e.g., $\lambda_N$=355 nm), the third sensor 142 may be configured to measure radiation above 360 nm. For instance, the third sensor 142 may sample radiation in the band 370-410 nm, which may correspond to at least a portion of the ultraviolet band corresponding to ultraviolet light generated by the ultraviolet excitation of one or more photoluminescent defects, which can be observed in the photoluminescence spectral data in FIG. 1B.

In another embodiment, optical element 120 of the system 100 may include a mirror for directing the third spectral range of radiation 113 toward the third sensor 142 for detecting UV photoluminescent radiation.

Figure 1I:
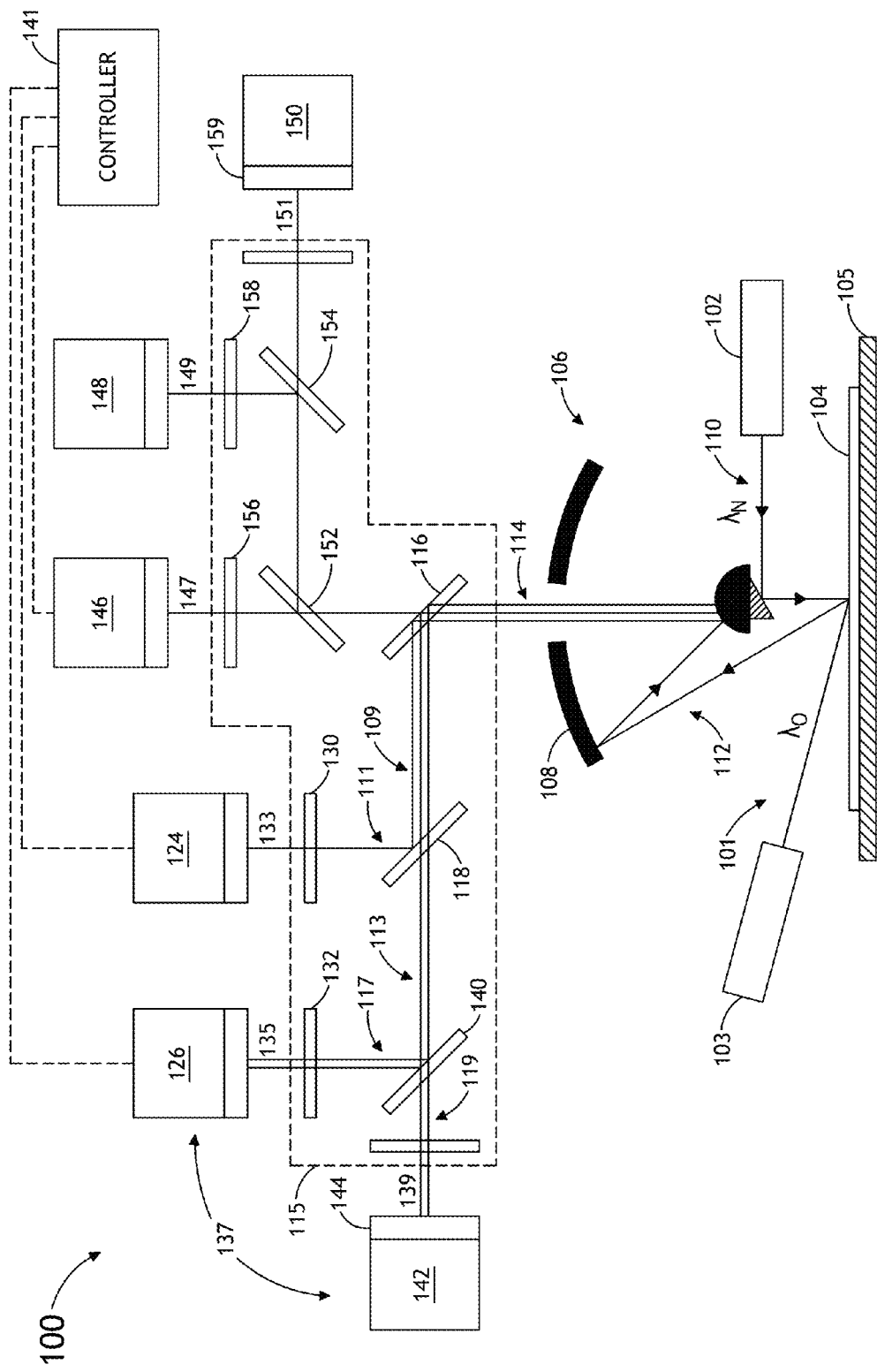
FIG. 1I illustrates a simplified schematic view of a system for defect detection and photoluminescence measurement of a sample, in accordance with one embodiment of the present invention.

FIG. 1I illustrates a block diagram view of system 100, in accordance with an alternative embodiment of the present invention. It is noted herein that the embodiments and examples described previously herein with respect to system 100 should be interpreted to extend to the embodiments of system 100 depicted in FIG. 1I unless otherwise noted.

It is further noted herein that the embodiment depicted in FIG. 1I serves to provide a number of photoluminescence spectral bins, each matched to a particular spectral signature of a type of stacking fault (e.g., bar-shaped stacking faults, 2S stacking faults and 4S stacking faults). This configuration further provides for the classification of stacking faults, in real-time or near-real-time.

Further, the embodiment depicted in FIG. 1I may achieve the type of spectral segmentation depicted in FIG. 1J below, which serves to isolate the characteristic photoluminescence bands into several distinct photoluminescence spectral bins. It is noted herein that some level of cross-talk may exist given the broad photoluminescent lines for each defect type in spectrum 160. It is further recognized, however, that a good balance between total signal and crosstalk reduction may be achieved by choosing the photoluminescence bins to roughly correspond to the full width half maximum (FWHM) of each radiative recombination line for each stacking fault type.

In one embodiment, the system 100 may be configured without the oblique-incidence radiation source 103 and corresponding sensor 126 and filter 132. In another embodiment, the controller 141 of system 100 may selectively activate and deactivate the oblique-incidence radiation source 103, as described previously herein. In yet another embodiment, the system 100 may include the oblique-incidence radiation source 103, as described previously herein. It is noted herein that the following description is provided in the context of the oblique-incidence light source 103 being including in system 100. It is further noted, however, that this is not a limitation and the system 100 may be embodied without the oblique-incidence radiation source 103.

As described previously herein, the filter sub-system 115 of system 100 is configured to receive at least a portion of the radiation collected by the set of collection optics 106.

In the case where the oblique-incidence source 103 is present, the filter sub-system 115 is further configured to separate the radiation into a portion 111 of radiation including the normal-illumination wavelength $\lambda_N$ and an additional portion 117 of radiation including the oblique-illumination wavelength $\lambda_O$, as described previously herein.

In another embodiment, the filter sub-system 115 is configured to separate the radiation 114 from the sample 104 into a plurality of portions of photoluminescent radiation. In another embodiment, each portion includes one or more wavelengths in a different spectral range of the radiation emitted by the one or more photoluminescing defects of the sample 104.

By way of example, the detection sub-system 137 may include, but is not limited to, a first PL sensor 146 for measuring one or more characteristics (e.g., intensity) of a first portion of PL radiation transmitted by the filter sub-system 115, a second PL sensor 150 for measuring one or more characteristics of a second portion of PL radiation transmitted by the filter sub-system 115, a third PL sensor 148 for receiving a third portion of PL radiation transmitted by the filter sub-system 115 and a fourth PL sensor 142 for receiving a fourth portion of PL radiation transmitted through the filter sub-system 115.

In another embodiment, as described previously herein, the detection sub-system 137 may further include a normal-scattering sensor 124 for receiving $\lambda_N$ radiation scattered from one or more defects of the sample 104 and an oblique-scattering sensor 126 for receiving $\lambda_O$ radiation scattered from one or more defects of the sample 104.

In one embodiment, each of the sensors described above may correspond with a particular spectral bin. In one embodiment, filter sub-system 115 includes a plurality of optical elements and a plurality of narrow band filters in order to separate the radiation received from the sample into a plurality of spectral bins.

In one embodiment, the plurality of optical elements may include, but is not limited to, optical elements 116, 118, 140, 152 and 154. For example, each of the optical elements 116, 118, 140, 152 and 154 may include, but are not limited to, a dichroic beam splitter (e.g., LWP filter), as described previously herein. It is recognized herein that each of the optical elements 116, 118, 140, 152 and 154 may serve to direct a given spectral range of radiation including a selected spectral band toward the corresponding sensor. In another embodiment, the plurality of narrow band filters may include, but is not limited to narrow band filters 130, 132, 156, 158, 159 and 144. It is recognized herein that each of the narrow band filters may serve to define a given spectral bin of the plurality of spectral bins by transmitting light included in the given spectral bin and blocking light outside the given spectral bin.

In one embodiment, the first PL sensor 146 is configured to receive radiation in a spectral band of 480-520 nm from the first narrow band filter 156. In another embodiment, the second PL sensor 150 is configured to receive radiation in a spectral band of 440-470 nm from the narrow band filter 159. In another embodiment, the third PL sensor 148 is configured to receive radiation in a spectral band of 410-435 nm from the narrow band filter 158. In one embodiment, the fourth PL sensor 142 is configured to receive radiation in a spectral band of 370-400 nm from the narrow band filter 144. In another embodiment, the normal-scattering sensor 124 may receive radiation in a spectral band of 350-360 nm from the narrow band filter 130, while the oblique-scatter sensor 126 may receive radiation in a spectral band of 400-410 nm from the narrow band filter 132.

In one embodiment, the optical elements and the plurality of narrow band filters are arranged to define the plurality of spectral bins according to a set of anticipated spectral characteristics of one or more photoluminescent defects of the sample. In another embodiment, the plurality of optical elements and the plurality of narrow band filters are arranged to substantially match the full width half maximum (FWHM) values to a set of corresponding intensity peaks of a photoluminescent spectrum 161. In one embodiment, as shown in FIG. 1J, a first spectral bin 162 (defined by filter 156 and sensor 146) may be matched to a first photoluminescence peak 163 (e.g., FWHM) indicative of the presence of a first type of stacking fault (e.g., 2S stacking faults). In another embodiment, as shown in FIG. 1H, a second spectral bin 164 (defined by filter 159 and sensor 150) may be matched to a second photoluminescence peak 165 (e.g., FWHM) indicative of the presence of a second type of stacking fault (e.g., 4S stacking faults). In another embodiment, as shown in FIG. 1J, a third spectral bin 166 (defined by filter 158 and sensor 148) may be matched to a third photoluminescence peak 167 (e.g., FWHM) indicative of the presence of a third type of stacking fault (e.g., bar-type stacking faults).

Figure 1J:
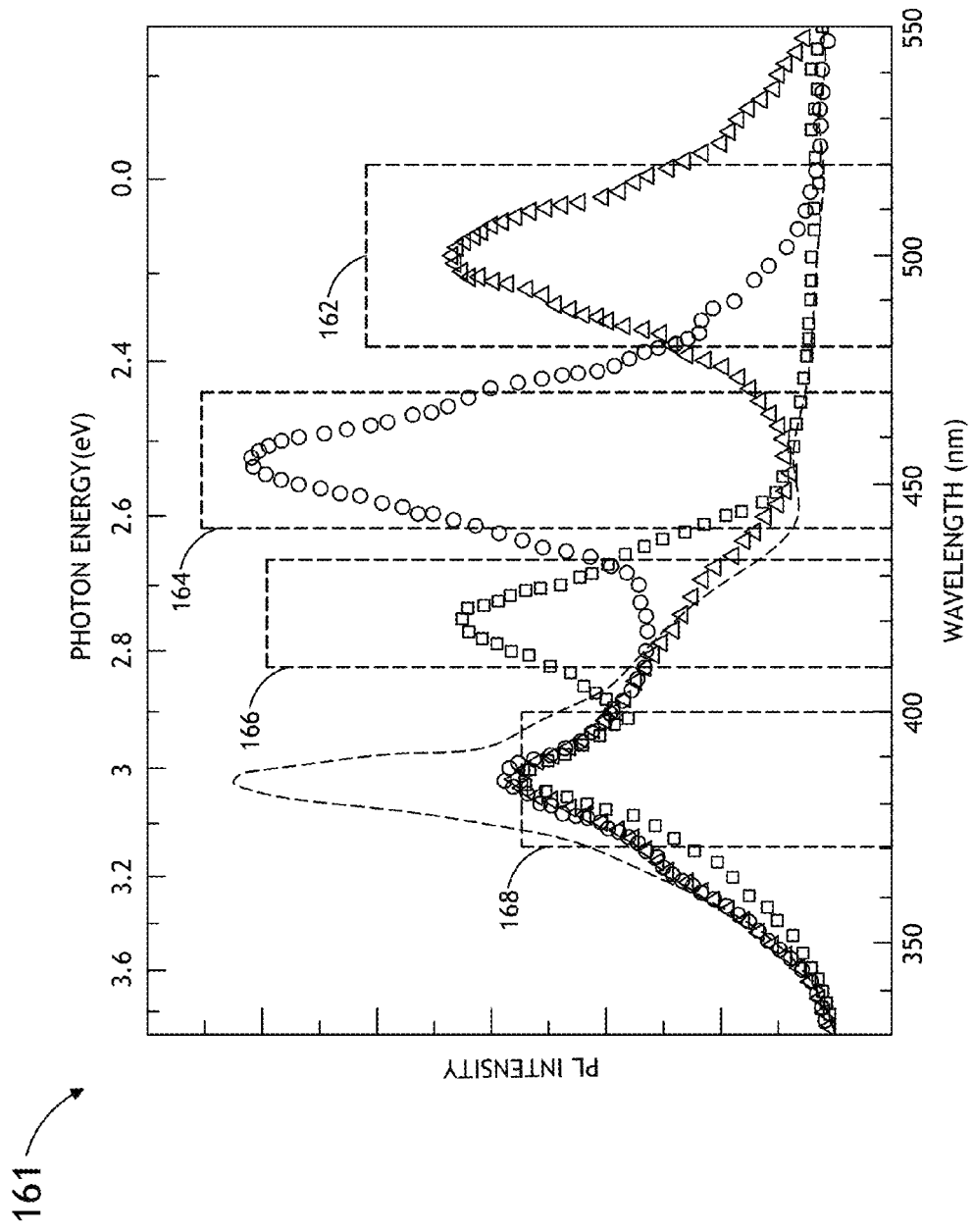
FIG. 1J illustrates a set of spectral integration bins superposed on a photoluminescent spectrum, in accordance with one embodiment of the present invention.

In another embodiment, as shown in FIG. 1J, a fourth spectral bin 168 (defined by filter 144 and sensor 142) may be matched to one or more fourth photoluminescence peaks 169 (e.g., FWHM). In the case of the photoluminescent spectrum 161 of FIG. 1J, the spectral bin 168 acts to measure a set of broad photoluminescent peaks indicative of the presence of each type of stacking fault defect described above.

In another embodiment, the control system 141 of system 100 may detect one or more photoluminescence defects based on the light detected by each of the plurality of sensors. In one embodiment, the control system 141 may detect the photoluminescence defects by comparing a signal from at least one of the plurality of sensors in an area of the sample absent of photoluminescing defects to a signal from at least one of the plurality of sensors acquired from a measured region of the sample. In this regard, each stacking fault type may be detected in dedicated spectral bins, each coupled to a dedicated sensor (e.g., PMT).

In another embodiment, the controller 141 may classify the one or more detected photoluminescence defects based on one or more signals measured by each of the plurality of sensors. In this regard, the controller 141 may classify each stacking fault defect based on the presence of photoluminescent signature wavelengths. It is noted herein that the implementation of the spectral bins of the present invention allows for fast and efficient photoluminescent defect classification in settings where the given defect(s) is too small for adequate identification via shape algorithms. It is understood that when the size of the photoluminescent-only defect is large enough to be properly sampled and represented in imagery data the system may further apply one or more shape identification algorithms to classify the given defect (e.g., triangle defect, bar defect and the like). It is further recognized that the embodiment depicted in FIG. 1I is not limited to the spectral bins explicitly noted above. Rather, the spectral bins discussed in the present disclosure have been provided merely for illustrative purposes. It is anticipated that additional spectral bin scenarios may be applicable within the scope of the present invention. For example, rather than three individual spectral bins (as shown in FIGS. 1I and 1J), the system 100 may carry out the classification process utilizing additional spectral bins. For instance, utilizing additional spectral bins, the controller 141 may classify defects based on the fact that a triangle stacking fault should have strong back level swing, whereas a bar-shaped stacking fault may have strong black level signature, and at the same time, a reduced white level signature. This difference in relative signal variations may be used for stacking fault classification using photoluminescence.

While the foregoing description has focused on oblique channel and normal channel photoluminescence defect (e.g., SF defect and basal plane dislocations) and scattering defect detection, it is recognized herein that the system 100 of the present invention may utilize additional architectures and configurations during implementation. In some embodiments, the system 100 may be equipped with autofocusing devices for carrying out an autofocus routine during inspection and detection of scattering defect and photoluminescence defects. In other embodiments, the system 100 of the present invention may be equipped with power control devices and systems for controlling the power of the light sources (e.g., oblique-incidence source 103 and normal-incidence source 102). For instance, the one or more power control devices may be used to control the power of light incident on the sample 104 for calibration or other purposes.

In other embodiments, the system 100 may include one or more oblique channels configured to measure reflected light from the sample. For instance, the system 100 may include additional light sources, optical focusing and control elements, and detection devices configured for measuring specular reflection of the sample, one or more slope channels, and/or one or more phase channels.

In other embodiments, the controller 141 of system 100 may retrieve signals from any of the various channels of the system 100 in order to classify one or more defects. For example, the controller 141 may receive signals from one or more of the following channels: oblique-incidence channel, normal-incidence channel, specular reflection channel, slope channel, phase channel and the like. Then, based on an analysis of the defect signatures in the data from one or more of these channels the controller 141 may classify a measured defect. For instance, the controller 141 may compare an image taken via a first channel in a first contrast mode and then compare that image to an image taken via a second channel (or an Nth channel) in an Nth contrast mode in order to classify one or more photoluminescence defects (e.g., SF defects or basal plane dislocations) of sample 104.

Figure 2:
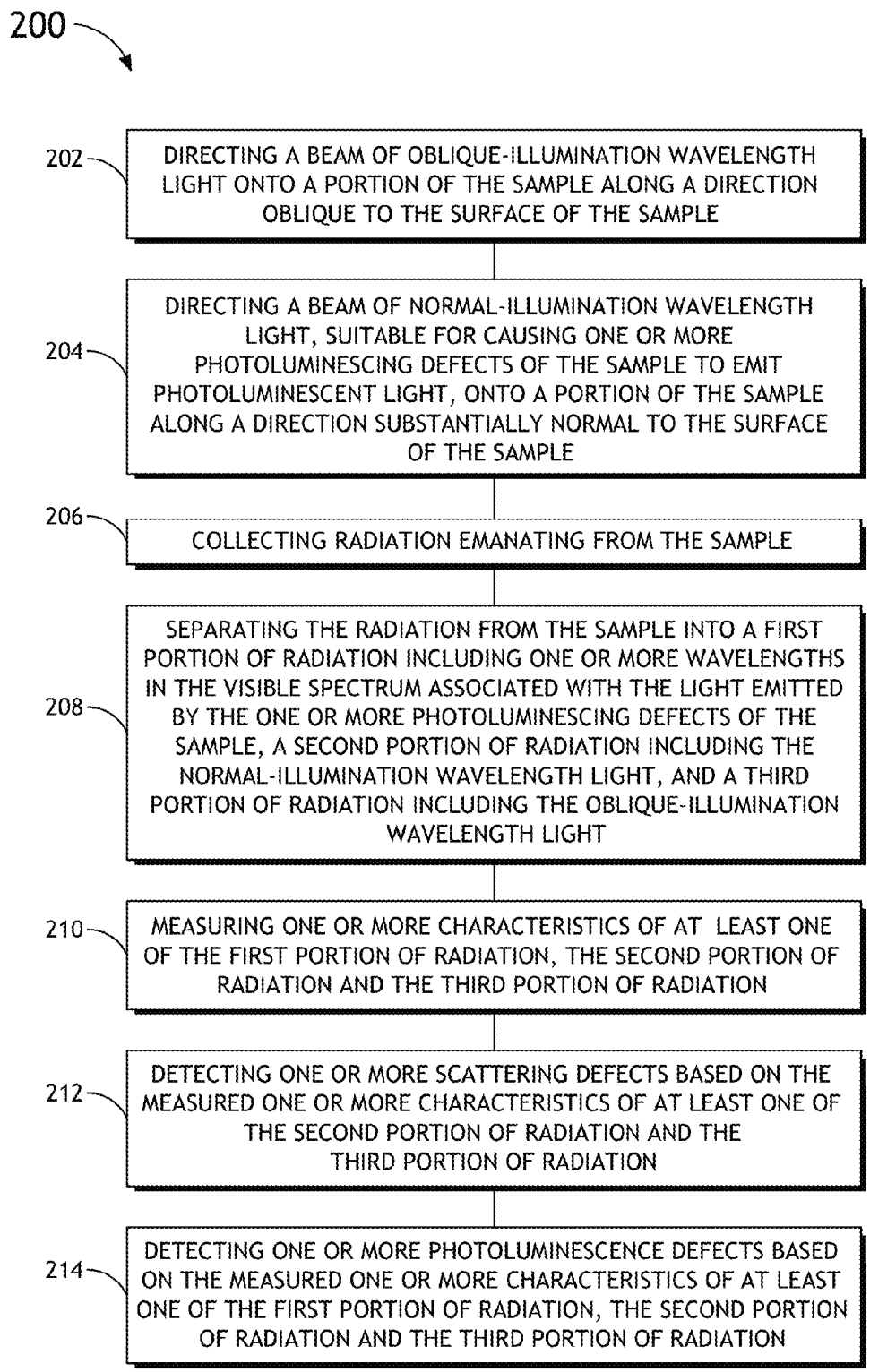
FIG. 2 is process flow diagram illustrating steps performed in a method for defect detection and photoluminescence measurement of a sample, in accordance with an embodiment of the present invention.

FIG. 2 illustrates a process flow diagram 200 depicting a method for defect detection and photoluminescence measurement of a sample. In step 202, a beam of oblique-illumination wavelength light is directed onto a portion of the sample along a direction oblique to the surface of the sample. In step 204, a beam of normal-illumination wavelength light is directed onto a portion of the sample along a direction substantially normal to the surface of the sample. In one embodiment, the beam of light of the normal-illumination wavelength is suitable for causing one or more photoluminescing defects of the sample to emit photoluminescent light. In step 206, radiation from the sample is collected. In one embodiment, the radiation from the sample including at least one of radiation elastically scattered by one or more defects of the sample or photoluminescence radiation emitted by the one or more photoluminescing defects of the sample. In step 208, the radiation from the sample is separated into a first portion of radiation including one or more wavelengths in the visible spectrum associated with the light emitted by the one or more photoluminescing defects of the sample, a second portion of radiation including the normal-illumination wavelength light, and at least a third portion of radiation including the oblique-illumination wavelength light. In step 210, one or more characteristics of at least one of the first portion of radiation, the second portion of radiation and the third portion of radiation are measured. In step 212, one or more scattering defects are detected based on the measured one or more characteristics of at least one of the second portion of radiation and the third portion of radiation. In step 214, one or more photoluminescence defects are detected based on the measured one or more characteristics of at least one of the first portion of radiation, the second portion of radiation and the third portion of radiation by comparing the one or more characteristics of at least one of the first portion of radiation, the second portion of radiation and the third portion of radiation acquired from an area of the sample absent of photoluminescing defects to one or more characteristics of at least one of the first portion of radiation, the second portion of radiation and the third portion of radiation acquired from a measured region of the sample.

Figure 3:
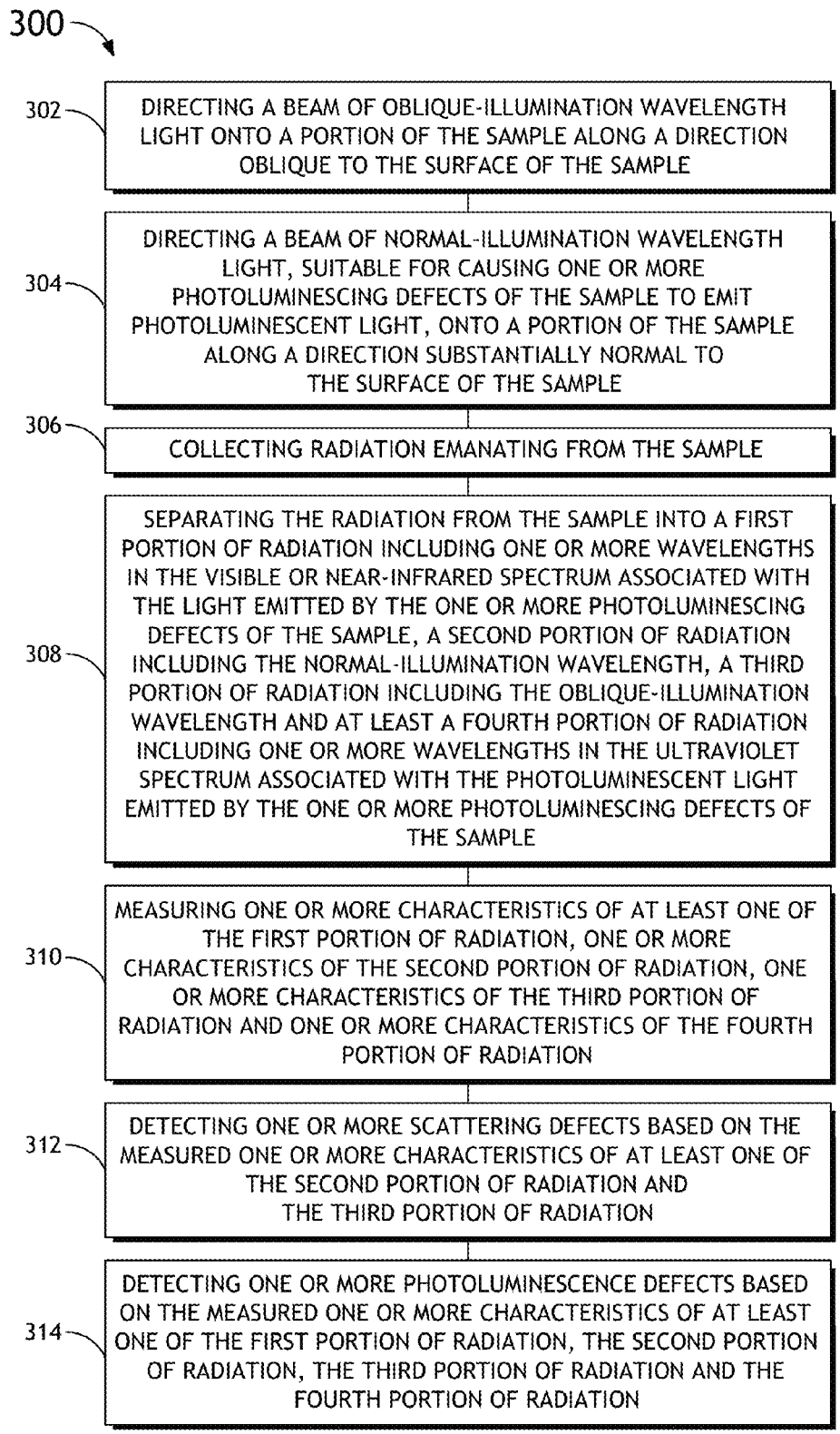
FIG. 3 is process flow diagram illustrating steps performed in a method for defect detection and photoluminescence measurement of a sample, in accordance with an embodiment of the present invention.

FIG. 3 illustrates a process flow diagram 300 depicting a method for defect detection and photoluminescence measurement of a sample. In step 302, a beam of oblique-illumination wavelength light is directed onto a portion of the sample along a direction oblique to the surface of the sample. In step 304, a beam of normal-illumination wavelength light is directed along a direction substantially normal to the surface of the sample. In one embodiment, the beam of light of the normal-illumination wavelength is suitable for causing one or more photoluminescing defects of the sample to emit photoluminescent light. In step 306, radiation from the sample is collected. In one embodiment, the radiation from the sample including at least one of radiation elastically scattered by one or more defects of the sample or photoluminescence radiation emitted by the one or more photoluminescing defects of the sample. In step 308, the radiation from the sample is separated into a first portion of radiation including one or more wavelengths in the visible or near-infrared spectrum associated with the light emitted by the one or more photoluminescing defects of the sample, a second portion of radiation including the normal-illumination wavelength, a third portion of radiation including the oblique-illumination wavelength and at least a fourth portion of radiation including one or more wavelengths in the ultraviolet spectrum associated with the photoluminescent light emitted by the one or more photoluminescing defects of the sample. In step 310, one or more characteristics of at least one of the first portion of radiation, one or more characteristics of the second portion of radiation, one or more characteristics of the third portion of radiation and one or more characteristics of the fourth portion of radiation are measured. In step 312, one or more scattering defects are detected based on the measured one or more characteristics of at least one of the second portion of radiation and the third portion of radiation. In step 314, one or more photoluminescence defects are detected based on the measured one or more characteristics of at least one of the first portion of radiation, the second portion of radiation, the third portion of radiation and the fourth portion of radiation by comparing the one or more characteristics of at least one of the first portion of radiation, the second portion of radiation, the third portion of radiation and the fourth portion of radiation acquired from an area of the sample absent of photoluminescing defects to one or more characteristics of at least one of the first portion of radiation, the second portion of radiation, the third portion of radiation and the fourth portion of radiation acquired from a measured region of the sample.

Figure 4:
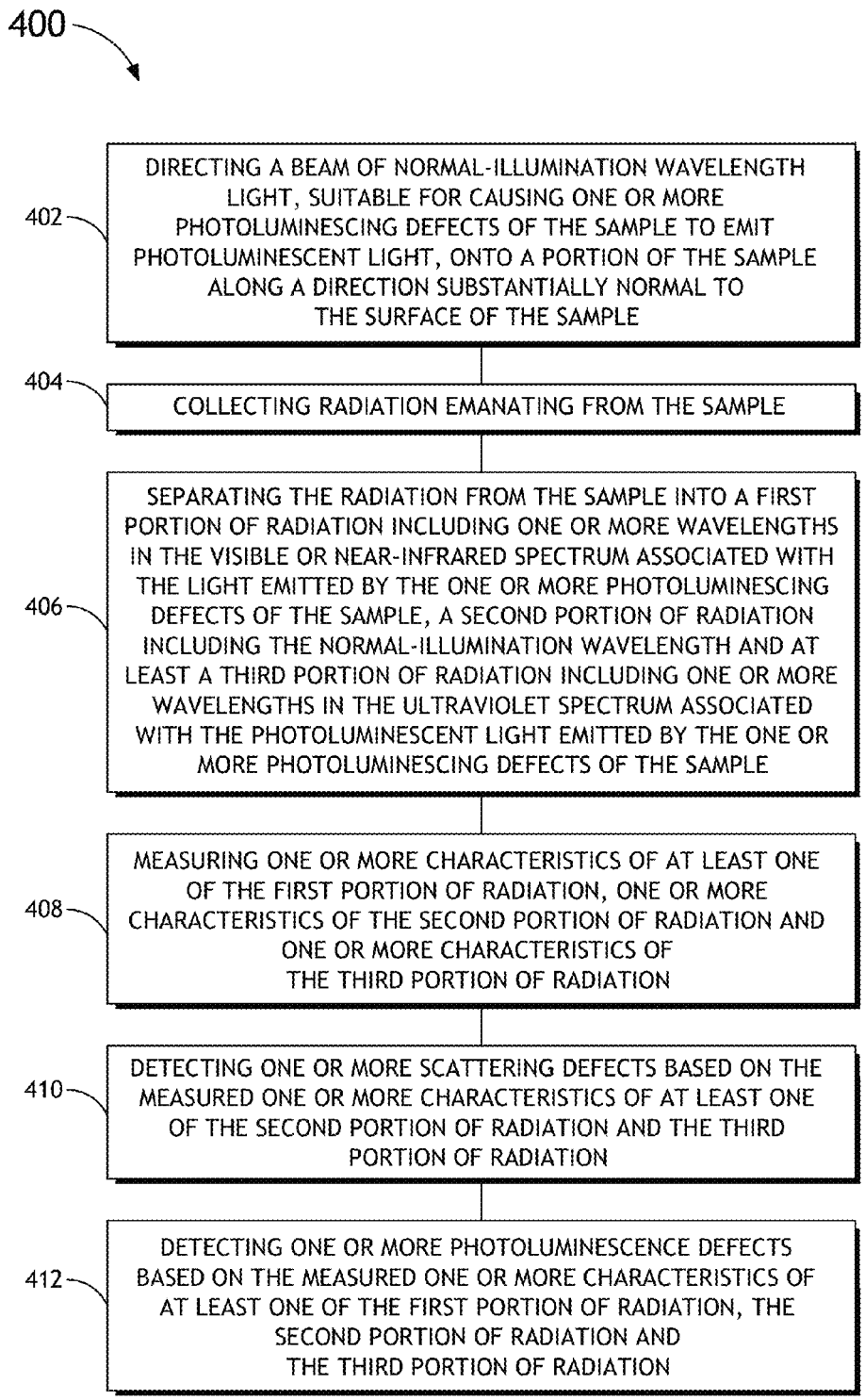
FIG. 4 is process flow diagram illustrating steps performed in a method for defect detection and photoluminescence measurement of a sample, in accordance with an embodiment of the present invention.

FIG. 4 illustrates a process flow diagram 400 depicting a method for defect detection and photoluminescence measurement of a sample. In step 402, a beam of normal-illumination wavelength light is directed along a direction substantially normal to the surface of the sample. In one embodiment, the beam of light of the normal-illumination wavelength is suitable for causing one or more photoluminescing defects of the sample to emit photoluminescent light. In step 404, radiation from the sample is collected. In one embodiment, the radiation from the sample including at least one of radiation elastically scattered by one or more defects of the sample or photoluminescence radiation emitted by the one or more photoluminescing defects of the sample. In step 406, radiation from the sample is separated into a first portion of radiation including one or more wavelengths in the visible or near-infrared spectrum associated with the light emitted by the one or more photoluminescing defects of the sample, a second portion of radiation including the normal-illumination wavelength and at least a third portion of radiation including one or more wavelengths in the ultraviolet spectrum associated with the photoluminescent light emitted by the one or more photoluminescing defects of the sample. In step 408, one or more characteristics of at least one of the first portion of radiation, one or more characteristics of the second portion of radiation and one or more characteristics of the third portion of radiation are measured. In step 410, one or more scattering defects are detected based on the measured one or more characteristics of at least one of the second portion of radiation and the third portion of radiation. In step 412, one or more photoluminescence defects are detected based on the measured one or more characteristics of at least one of the first portion of radiation, the second portion of radiation, and the third portion of radiation by comparing the one or more characteristics of at least one of the first portion of radiation, the second portion of radiation and the third portion of radiation acquired from an area of the sample absent of photoluminescing defects to one or more characteristics of at least one of the first portion of radiation, the second portion of radiation and the third portion of radiation acquired from a measured region of the sample.

Figure 5:
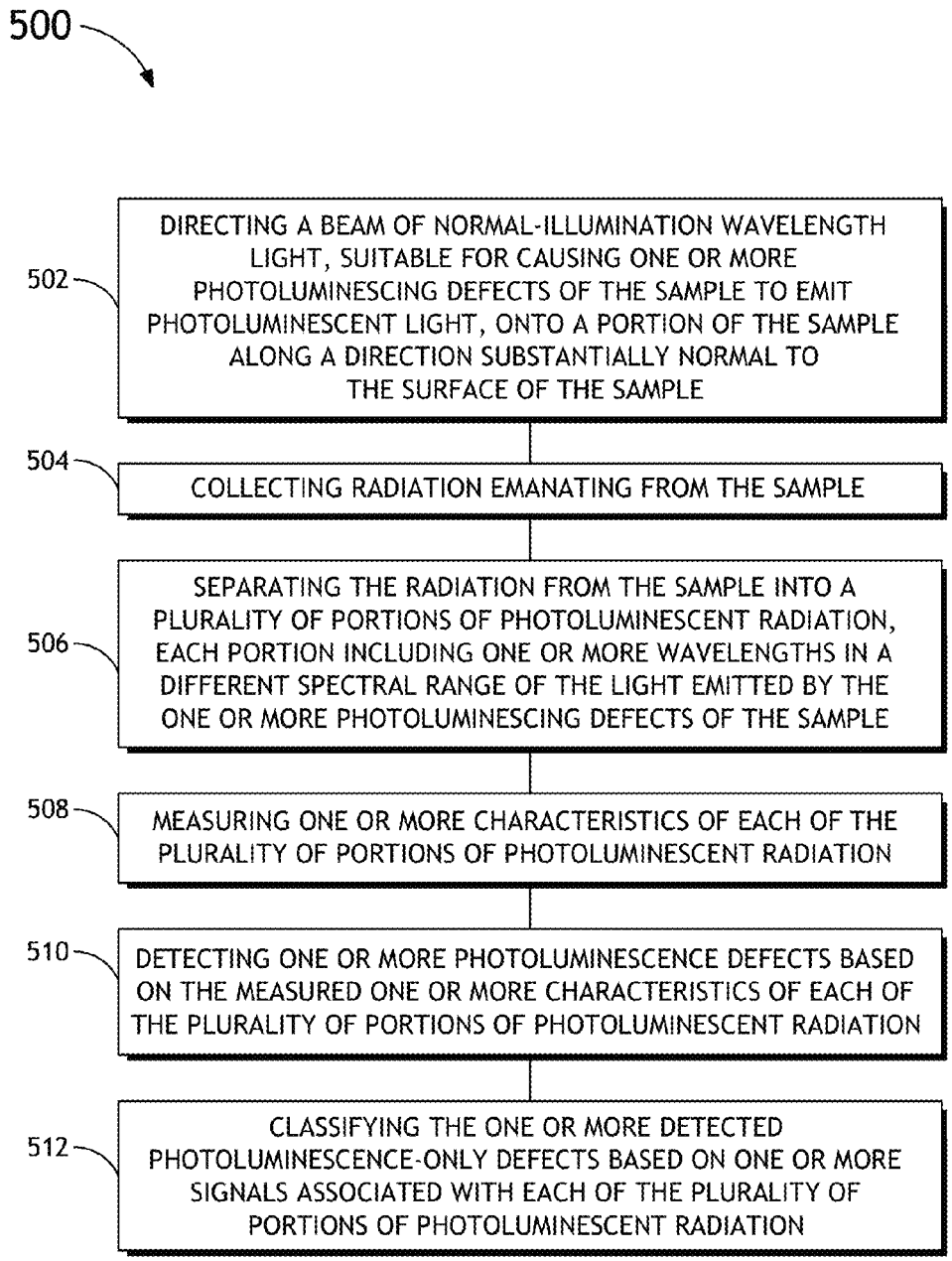
FIG. 5 is process flow diagram illustrating steps performed in a method for defect detection and photoluminescence measurement of a sample, in accordance with an embodiment of the present invention.

FIG. 5 illustrates a process flow diagram 500 depicting a method for defect detection and photoluminescence measurement of a sample. In step 502, a beam of normal-illumination wavelength light is directed onto a portion of the sample along a direction substantially normal to the surface of the sample. In one embodiment, the beam of light of the normal-illumination wavelength is suitable for causing one or more photoluminescing defects of the sample to emit photoluminescent light. In step 504, radiation from the sample is collected. In one embodiment, the radiation from the sample including at least one of radiation elastically scattered by one or more defects of the sample or photoluminescence radiation emitted by the one or more photoluminescing defects of the sample. In step 506, the radiation from the sample is separated into a plurality of portions of photoluminescent radiation, each portion including one or more wavelengths in a different spectral range of the light emitted by the one or more photoluminescing defects of the sample. In step 508, one or more characteristics of each of the plurality of portions of photoluminescent radiation are measured. In step 510, one or more photoluminescence defects are detected based on the measured one or more characteristics of each of the plurality of portions of photoluminescent radiation. In step 512, the one or more detected photoluminescence defects are classified based on one or more signals associated with each of the plurality of portions of photoluminescent radiation.

Figure 6:
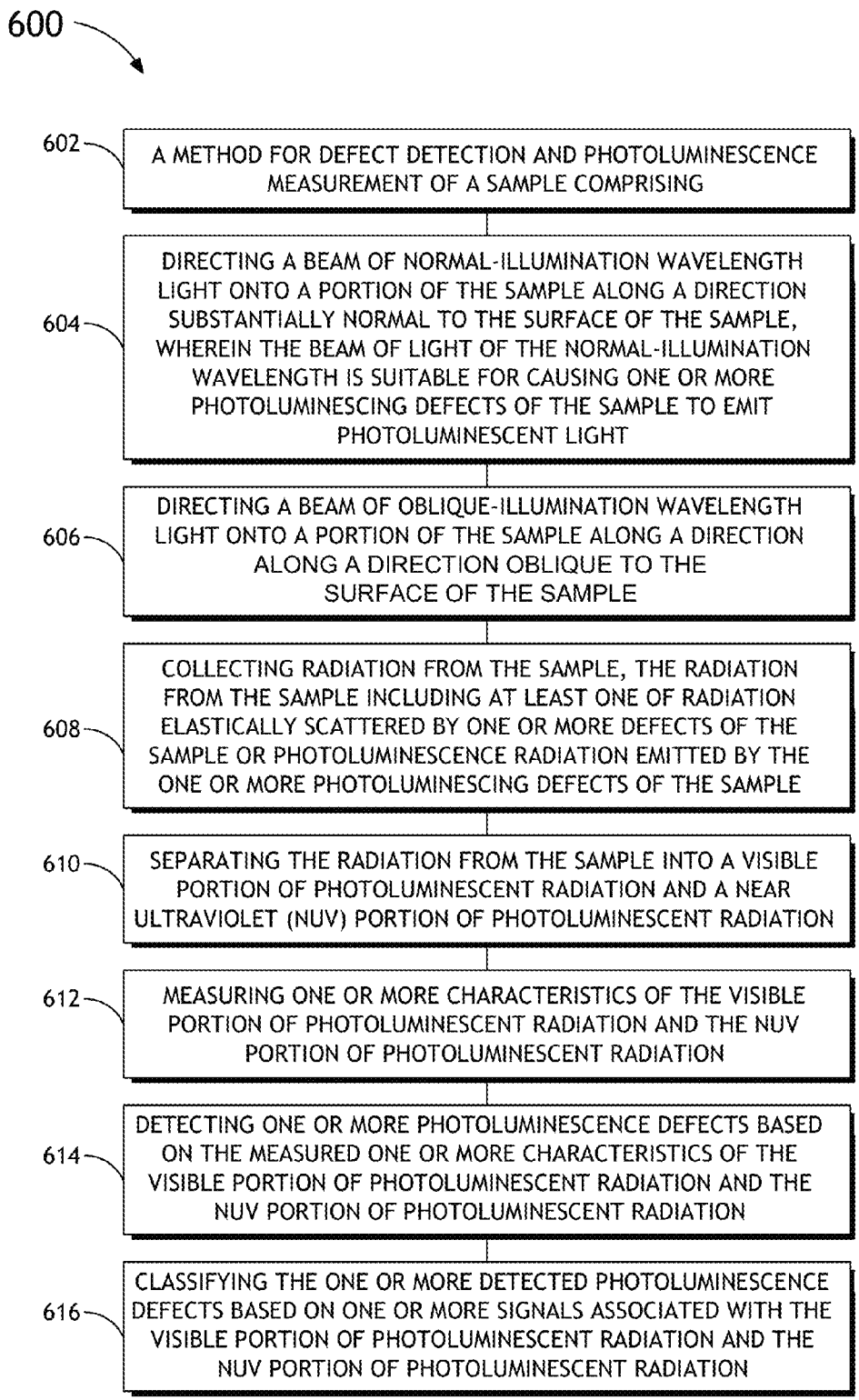
FIG. 6 is process flow diagram illustrating steps performed in a method for defect detection and photoluminescence measurement of a sample, in accordance with an embodiment of the present invention.

FIG. 6 illustrates a process flow diagram 600 depicting a method for defect detection and photoluminescence measurement of a sample. In step 602, a beam of normal-illumination wavelength light is directed onto a portion of the sample along a direction substantially normal to the surface of the sample. In one embodiment, the beam of light of the normal-illumination wavelength is suitable for causing one or more photoluminescing defects of the sample to emit photoluminescent light. In step 604, a beam of oblique-illumination wavelength light is directed onto a portion of the sample along a direction along a direction oblique to the surface of the sample. In step 606, radiation from the sample is collected. In one embodiment, the radiation from the sample includes at least one of radiation elastically scattered by one or more defects of the sample or photoluminescence radiation emitted by the one or more photoluminescing defects of the sample. In step 608, the radiation from the sample is separated into a visible portion of photoluminescent radiation and a near ultraviolet (NUV) portion of photoluminescent radiation. In step 610, one or more characteristics of the visible portion of photoluminescent radiation and the NUV portion of photoluminescent radiation are measured. In step 612, one or more photoluminescence defects are detected based on the measured one or more characteristics of the visible portion of photoluminescent radiation and the NUV portion of photoluminescent radiation. In step 614, the one or more detected photoluminescence defects are classified based on one or more signals associated with the visible portion of photoluminescent radiation and the NUV portion of photoluminescent radiation.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A system for defect detection and photoluminescence measurement of a sample comprising:
   an oblique-incidence radiation source configured to direct a beam of light of an oblique-illumination wavelength onto a portion of the sample along a direction oblique to the surface of the sample;
   a normal-incidence radiation source configured to direct a beam of light of a normal-illumination wavelength different from the oblique-illumination wavelength onto a portion of the sample along a direction substantially normal to the surface of the sample, wherein the beam of light of the normal-illumination wavelength is suitable for causing one or more photoluminescing defects of the sample to emit photoluminescent light;
   a sample stage assembly configured to secure the sample and selectively actuate the sample in order to perform a scanning process with at least the oblique-incidence radiation source and the normal-incidence radiation source;
   a set of collection optics configured to collect radiation from the sample, the radiation from the sample including at least one of radiation elastically scattered by one or more defects of the sample or photoluminescence radiation emitted by the one or more photoluminescing defects of the sample;
   a filter sub-system configured to receive at least a portion of the radiation collected by the set of collection optics, wherein the filter sub-system is configured to separate the radiation from the sample into a first portion of radiation including one or more wavelengths in the visible or near-infrared spectrum associated with the light emitted by the one or more photoluminescing defects of the sample, a second portion of radiation including the normal-illumination wavelength, and at least a third portion of radiation including the oblique-illumination wavelength;
   a detection sub-system including a first sensor for measuring one or more characteristics of the first portion of radiation transmitted by the filter sub-system, a second sensor for measuring one or more characteristics of the second portion of radiation transmitted by the filter sub-system and at least a third sensor for measuring one or more characteristics of the third portion of radiation transmitted by the filter sub-system; and
   a controller communicatively coupled to the first sensor, the second sensor and the third sensor, the controller configured to:
      detect one or more scattering defects based on at least one of the one or more characteristics measured by the one or more characteristics measured by the second sensor and the third sensor; and
      detect one or more photoluminescence defects based on at least one of the one or more characteristics measured by the first sensor, the one or more characteristics measured by the second sensor and the one or more characteristics measured by the third sensor.

2. The system of claim 1, wherein the controller is further configured to detect one or more photoluminescence defects based on at least one of the one or more characteristics measured by the first sensor, the one or more characteristics measured by the second sensor and the one or more characteristics measured by the third sensor by comparing a signal from at least one of the first sensor, the second sensor and the third sensor in an area of the sample absent of photoluminescing defects to a signal from at least one of the first sensor, the second sensor and the third sensor acquired from a measured region of the sample.

3. The system of claim 1, wherein the controller is further configured to map the detected one or more photoluminescence defects based on at least one of the one or more characteristics measured by the first sensor, the one or more characteristics measured by the second sensor and the one or more characteristics measured by the third sensor and a position of the detected one or more photoluminescence defects.

4. The system of claim 1, wherein the controller is further configured to classify the detected one or more photoluminescence defects based on at least one of the one or more characteristics measured by the first sensor, the one or more characteristics measured by the second sensor and the one or more characteristics measured by the third sensor.

5. The system of claim 1, wherein the one or more photoluminescing defects of the sample comprise:
   at least one of one or more stacking fault defects and one or more basal plane dislocations.

6. The system of claim 1, wherein the controller is further configured to differentiate the detected one or more scattering defects as pit defects or particle defects based on the light detected by at least one of the second and third sensors.

7. The system of claim 1, wherein the controller is configured to selectably deactivate the first radiation source prior to at least one of measurement of the second portion of radiation by the second sensor and measurement of the third portion of radiation by the third sensor in order to detect one or more photoluminescence defects based on the light detected by at least one of the second sensor and the third sensor.

8. The system of claim 1, wherein the sample is a semiconductor device.

9. The system of claim 8, wherein the semiconductor device is a wide-bandgap semiconductor device.

10. The system of claim 1, wherein at least one of the oblique-incidence source and the normal-incidence source is a laser.

11. The system of claim 1, wherein at least one of the oblique-incidence source and the normal-incidence source is an ultraviolet laser.

12. The system of claim 1, wherein at least one of the oblique-incidence source and the normal-incidence source is a continuous wave (CW) laser.

13. The system of claim 1, wherein the sample stage assembly configured to secure the sample and selectively actuate the sample in order to perform a scanning process with at least the oblique-incidence radiation source and the normal-incidence radiation source comprises:
a rotational stage assembly configured to secure the sample and selectively rotate the sample in order to perform a spiral scanning process with at least the oblique-incidence radiation source and the normal-incidence radiation source.

14. The system of claim 1, wherein the sample stage assembly configured to secure the sample and selectively actuate the sample in order to perform a scanning process with at least the oblique-incidence radiation source and the normal-incidence radiation source comprises:
a linear stage assembly configured to secure the sample and selectively translate the sample along at least a first direction and a second direction perpendicular to the first direction in order to perform an X-Y scanning process with at least the oblique-incidence radiation source and the normal-incidence radiation source.

15. The system of claim 1, wherein the filter sub-system includes:
a first optical element configured to separate a first spectral range of radiation including the first portion of radiation from the radiation received from the sample and direct the first spectral range of radiation toward the first sensor;
a second optical element configured to receive radiation from the first optical element not included in the first spectral range of radiation, wherein the second optical element is configured to separate a second spectral range of radiation including the second portion of radiation from the radiation received from the first optical element and direct the second spectral range of radiation toward the second sensor; and
a third optical element configured to receive radiation from the second optical element not included in the first spectral range of radiation or the second spectral range of radiation, wherein the third optical element is configured to at least direct a portion of a third spectral range of radiation including the third portion of radiation toward the third sensor.

16. The system of claim 15, wherein at least one of the first optical element and the second optical element is a dichroic beam splitter and the third optical element is a mirror.

17. The system of claim 16, wherein the filter sub-system includes:
a first optical element configured to separate a first spectral range of radiation including the first portion of radiation from the radiation received from the sample and direct the first spectral range of radiation toward the first sensor;
a second optical element configured to receive radiation from the first optical element not included in the first spectral range of radiation, wherein the second optical element is configured to separate a second spectral range of radiation including the second portion of radiation from the radiation received from the first optical element and direct the second spectral range of radiation toward the second sensor; and
a third optical element configured to receive radiation from the second optical element not included in the first spectral range of radiation or the second spectral range of radiation, wherein the third optical element is configured to at least separate a portion of a third spectral range of radiation including the third portion of radiation from the radiation received from the second optical element and direct the third spectral range of radiation toward the third sensor, the third optical element further configured to transmit radiation not included in the first spectral range of radiation, the second spectral range of radiation or the third spectral range of radiation to one or more additional optical devices.

18. The system of claim 17, wherein at least one of the first optical element and the second optical element and the third optical element is a dichroic beam splitter.

19. The system of claim 16, further comprising:
a first narrow pass filter positioned between the first sensor and the first optical element and configured to receive at least a portion of the first spectral range of radiation and transmit the first portion of radiation to the first sensor and block radiation not included in the first portion of radiation;
a second narrow pass filter positioned between the second sensor and the second optical element configured to receive at least a portion of the second spectral range of radiation and transmit the second portion of radiation to the second sensor and block radiation not included in the second portion of radiation; and
a third narrow pass filter positioned between the third sensor and the third optical element configured to receive at least a portion of the third spectral range of radiation and transmit the third portion of radiation to the third sensor and block radiation not included in the third portion of radiation.

20. The system of claim 19, wherein the spectral range transmitted by at least one of the first narrow pass filter, the second narrow pass filter and the third narrow pass filter is defined by one or more characteristics of the photoluminescence spectrum of features of the sample.

21. The system of claim 1, wherein at least one of the first sensor, the second sensor and the third sensor includes a photomultiplier tube (PMT).

22. The system of claim 1, wherein the first sensor is configured to measure at least one of visible photoluminescence light and near-infrared light emitted from one or more photoluminescent defects of the sample.

23. The system of claim 1, wherein the second sensor is configured to measure scattered radiation from one or more defects of the sample at a wavelength corresponding with the light emitted by the normal-incidence radiation source.

24. The system of claim 1, wherein the third sensor is configured to measure scattered radiation from one or more defects of the sample at a wavelength corresponding with the light emitted by the oblique-incidence radiation source.

25. The system of claim 1, wherein at least one of the second sensor and third sensor is configured to measure ultraviolet photoluminescence light from one or more photoluminescent defects of the sample.

26. The system of claim 1, wherein the system is configured to detect photoluminescence defects and scattering defects simultaneously or sequentially.

27. A system for defect detection and photoluminescence measurement of a sample comprising:

an oblique-incidence radiation source configured to direct a beam of light of an oblique-illumination wavelength onto a portion of the sample along a direction oblique to the surface of the sample;

a normal-incidence radiation source configured to direct a beam of light of a normal-illumination wavelength different from the oblique-illumination wavelength onto a portion of the sample along a direction substantially normal to the surface of the sample, wherein the beam of light of the normal-illumination wavelength is suitable for causing one or more photoluminescing defects of the sample to emit photoluminescent light;

a sample stage assembly configured to secure the sample and selectively actuate the sample in order to perform a scanning process with at least the oblique-incidence radiation source and the normal-incidence radiation source;

a set of collection optics configured to collect radiation from the sample, the radiation from the sample including at least one of radiation elastically scattered by one or more defects of the sample or photoluminescence radiation emitted by the one or more photoluminescing defects of the sample;

a filter sub-system configured to receive at least a portion of the radiation collected by the set of collection optics, wherein the filter sub-system is configured to separate the radiation from the sample into a first portion of radiation including one or more wavelengths in the visible or near-infrared spectrum associated with the light emitted by the one or more photoluminescing defects of the sample, a second portion of radiation including the normal-illumination wavelength, a third portion of radiation including the oblique-illumination wavelength and at least a fourth portion of radiation including one or more wavelengths in the ultraviolet spectrum associated with the photoluminescent light emitted by the one or more photoluminescing defects of the sample;

a detection sub-system including a first sensor for measuring one or more characteristics of the first portion of radiation transmitted by the filter sub-system, a second sensor for measuring one or more characteristics of the second portion of radiation transmitted by the filter sub-system, a third sensor for measuring one or more characteristics of the third portion of radiation transmitted by the filter sub-system and at least a fourth sensor for measuring one or more characteristics of the fourth portion of radiation transmitted by the filter sub-system; and a controller communicatively coupled to the first sensor, the second sensor and the third sensor, the controller configured to:

detect one or more scattering defects based on the light measured by at least one of the second sensor and the third sensor; and detect one or more photoluminescence defects based on the light detected by at least one of the first sensor, the second sensor, the third sensor and the fourth sensor by comparing a signal from at least one of the first sensor, the second sensor, the third sensor and the fourth sensor in an area of the sample absent of photoluminescing defects to a signal from at least one of the first sensor, the second sensor, the third sensor and the fourth sensor acquired from a measured region of the sample.

28. The system of claim 27, wherein the one or more photoluminescing defects of the sample comprise:
at least one of one or more stacking fault defects and one or more basal plane dislocations.

29. The system of claim 27, wherein the controller is further configured to differentiate the detected one or more scattering defects as pit defects or particle defects based on the light detected by at least one of the second and third sensors.

30. The system of claim 27, wherein the filter sub-system includes:

a first optical element configured to separate a first spectral range of radiation including the first portion of radiation from the radiation received from the sample and direct the first spectral range of radiation toward the first sensor;

a second optical element configured to receive radiation from the first optical element not included in the first spectral range of radiation, wherein the second optical element is configured to separate a second spectral range of radiation including the second portion of radiation from the radiation received from the first optical element and direct the second spectral range of radiation toward the second sensor; and a third optical element configured to receive radiation from the second optical element not included in the first spectral range of radiation or the second spectral range of radiation, wherein the third optical element is configured to at least separate a portion of a third spectral range of radiation including the third portion of radiation from the radiation received from the second optical element and direct the third spectral range of radiation toward the third sensor, the third optical element further configured to transmit radiation not included in the first spectral range of radiation, the second spectral range of radiation or the third spectral range of radiation toward the fourth sensor in a fourth spectral range of radiation including the fourth portion of radiation.

31. The system of claim 30, wherein at least one of the first optical element, the second optical element and the third optical element is a dichroic beam splitter.

32. The system of claim 30, further comprising:

a first narrow pass filter positioned between the first sensor and the first optical element and configured to receive at least a portion of the first spectral range of radiation and transmit the first portion of radiation to the first sensor and block radiation not included in the first portion of radiation;

a second narrow pass filter positioned between the second sensor and the second optical element configured to receive at least a portion of the second spectral range of radiation and transmit the second portion of radiation to the second sensor and block radiation not included in the second portion of radiation;

a third narrow pass filter positioned between the third sensor and the third optical element configured to receive at least a portion of the third spectral range of radiation and transmit the third portion of radiation to the third sensor and block radiation not included in the third portion of radiation; and a fourth narrow pass filter positioned between the fourth sensor and the third optical element configured to receive at least a portion of the fourth spectral range of radiation and transmit the fourth portion of radiation to the fourth sensor and block radiation not included in the fourth portion of radiation.

33. The system of claim 27, wherein at least one of the first sensor, the second sensor, the third sensor and the fourth sensor includes a photomultiplier tube (PMT).

34. The system of claim 27, wherein the controller is further configured to classify the detected one or more photoluminescence defects based on one or more spectral characteristics of light detected by at least one of the first sensor, the second sensor, the third sensor and the fourth sensor.

35. The system of claim 27, wherein the sample is a semiconductor device.

36. The system of claim 35, wherein the semiconductor device is a wide-bandgap semiconductor device.

37. The system of claim 27, wherein at least one of the oblique-incidence source and the normal-incidence source is a laser.

38. The system of claim 37, wherein at least one of the oblique-incidence source and the normal-incidence source is an ultraviolet laser.

39. The system of claim 38, wherein at least one of the oblique-incidence source and the normal-incidence source is a continuous wave (CW) laser.

40. The system of claim 27, wherein the sample stage assembly configured to secure the sample and selectively actuate the sample in order to perform a scanning process with at least the oblique-incidence radiation source and the normal-incidence radiation source comprises:
    a rotational stage assembly configured to secure the sample and selectively rotate the sample in order to perform a spiral scanning process with at least the oblique-incidence radiation source and the normal-incidence radiation source.

41. The system of claim 27, wherein the sample stage assembly configured to secure the sample and selectively actuate the sample in order to perform a scanning process with at least the oblique-incidence radiation source and the normal-incidence radiation source comprises:
    a linear stage assembly configured to secure the sample and selectively translate the sample along at least a first direction and a second direction perpendicular to the first direction in order to perform an X-Y scanning process with at least the oblique-incidence radiation source and the normal-incidence radiation source.

42. The system of claim 27, wherein the first sensor is configured to measure at least one of visible photoluminescence light and near-infrared light emitted from one or more photoluminescent defects of the sample and the fourth sensor is configured to measure ultraviolet photoluminescence light.

43. The system of claim 27, wherein the second sensor is configured to measure scattered radiation from one or more defects of the sample at a wavelength corresponding with the light emitted by the normal-incidence radiation source.

44. The system of claim 27, wherein the third sensor is configured to measure scattered radiation from one or more defects of the sample at a wavelength corresponding with the light emitted by the oblique-incidence radiation source.

45. The system of claim 27, wherein at least one of the second sensor and third sensor is configured to measure ultraviolet photoluminescence light from one or more photoluminescent defects of the sample.

46. The system of claim 27, wherein the system is configured to detect photoluminescence defects and scattering defects simultaneously or sequentially.

47. A system for defect detection and photoluminescence measurement of a sample comprising:
    a normal-incidence radiation source configured to direct a beam of light of a normal-illumination wavelength onto a portion of the sample along a direction substantially normal to the surface of the sample, wherein the beam of light of the normal-illumination wavelength is suitable for causing one or more photoluminescing defects of the sample to emit photoluminescent light;
    a sample stage assembly configured to secure the sample and selectively actuate the sample in order to perform a scanning process with at least the oblique-incidence radiation source and the normal-incidence radiation source;
    a set of collection optics configured to collect radiation from the sample, the radiation from the sample including at least one of radiation elastically scattered by one or more defects of the sample or photoluminescence radiation emitted by the one or more photoluminescing defects of the sample;
    a filter sub-system configured to receive at least a portion of the radiation collected by the set of collection optics, wherein the filter sub-system is configured to separate the radiation from the sample into a first portion of radiation including one or more wavelengths in the visible or near-infrared spectrum associated with the light emitted by the one or more photoluminescing defects of the sample, a second portion of radiation including the normal-illumination wavelength, and at least a third portion of radiation including one or more wavelengths in the ultraviolet spectrum associated with the light emitted by the one or more photoluminescing defects of the sample;
    a detection sub-system including a first sensor for measuring one or more characteristics of the first portion of radiation transmitted by the filter sub-system, a second sensor for measuring one or more characteristics of the second portion of radiation transmitted by the filter sub-system and at least a third sensor for measuring one or more characteristics of the third portion of radiation transmitted by the filter sub-system; and
    a controller communicatively coupled to the first sensor, the second sensor and the third sensor, the controller configured to:
        detect one or more scattering defects based on the light measured by the second sensor; and
        detect one or more photoluminescence defects based on the light detected by at least one of the first sensor and the third sensor by comparing a signal from at least one of the first sensor and the third sensor in an area of the sample absent of photoluminescing defects to a signal from at least one of the first sensor and the third sensor acquired from a measured region of the sample.

48. The system of claim 47, wherein at least one of the second sensor and third sensor is configured to measure ultraviolet photoluminescence light or near ultraviolet photoluminescence light from one or more photoluminescent defects of the sample.

49. A system for defect detection and photoluminescence measurement of a sample comprising:
    a normal-incidence radiation source configured to direct a beam of light of a normal-illumination wavelength onto a portion of the sample along a direction substantially normal to the surface of the sample, wherein the beam of light of the normal-illumination wavelength is suitable for causing one or more photoluminescing defects of the sample to emit photoluminescent light;
    a sample stage assembly configured to secure the sample and selectively actuate the sample in order to perform a scanning process with at least the oblique-incidence radiation source and the normal-incidence radiation source;
    a set of collection optics configured to collect radiation from the sample, the radiation from the sample including at least one of radiation elastically scattered by one or more defects of the sample or photoluminescence radiation emitted by the one or more photoluminescing defects of the sample;

a filter sub-system configured to receive at least a portion of the radiation collected by the set of collection optics, wherein the filter sub-system is configured to separate the radiation from the sample into a plurality of portions of photoluminescent radiation, each portion including one or more wavelengths in a different spectral range of the radiation emitted by the one or more photoluminescing defects of the sample;

a detection sub-system including a plurality of sensors, each sensor suitable for measuring one or more characteristics of one of the plurality of portions of photoluminescent radiation transmitted by the filter sub-system; and a controller communicatively coupled to each of the plurality of sensors, the controller configured to:
detect one or more photoluminescence defects based on the light detected by each of the plurality of sensors by comparing a signal from at least one of the plurality of sensors in an area of the sample absent of photoluminescing defects to a signal from at least one of the plurality of sensors acquired from a measured region of the sample; and
classify the one or more detected photoluminescence defects based on one or more signals measured by each of the plurality of sensors.

50. The system of claim 49, wherein the filter sub-system includes a plurality of optical elements and a plurality of narrow band filters in order to separate the radiation received from the sample into at least one of a plurality of NUV spectral bins, a plurality of UV bins and a plurality of visible spectral bins.

51. The system of claim 49, further comprising:
an oblique-incidence radiation source configured to direct a beam of light of an oblique-illumination wavelength onto a portion of the sample along a direction oblique to the surface of the sample.

52. The system of claim 51, wherein the filter sub-system is further configured to separate the radiation into at least one of a portion of radiation including the normal-illumination wavelength and at least an additional portion of radiation including the oblique-illumination wavelength.

53. The system of claim 52, wherein the detection sub-system includes at least one of a sensor suitable for measuring one or more characteristics of the portion of radiation including the normal-illumination wavelength transmitted by the filter sub-system and an additional sensor suitable for measuring the at least an additional portion of radiation including the oblique-illumination wavelength transmitted by the filter sub-system.

54. The system of claim 53, wherein the controller is further configured to detect one or more scattering defects based on the light measured by at least one of the sensor suitable for measuring one or more characteristics of the portion of radiation including the normal-illumination wavelength and the additional sensor suitable for measuring the at least an additional portion of radiation including the oblique-illumination wavelength.

55. The system of claim 49, wherein the filter sub-system includes a plurality of optical elements and a plurality of narrow band filters in order to separate the radiation received from the sample into a plurality of spectral bins.

56. The system of claim 55, wherein the plurality of optical elements and the plurality of narrow band filters define each of the plurality of spectral bins according to one or more anticipated spectral characteristics of one or more photoluminescent defects of the sample.

57. The system of claim 56, wherein the plurality of optical elements and the plurality of narrow band filters substantially match a plurality of full width half maximum values to a set of corresponding intensity peaks of a photoluminescent spectrum, wherein each intensity peak is indicative of the presence of a type of stacking fault.

58. A method for defect detection and photoluminescence measurement of a sample comprising:
directing a beam of oblique-illumination wavelength light onto a portion of the sample along a direction oblique to the surface of the sample;
directing a beam of normal-illumination wavelength light onto a portion of the sample along a direction substantially normal to the surface of the sample, wherein the beam of light of the normal-illumination wavelength is suitable for causing one or more photoluminescing defects of the sample to emit photoluminescent light;
collecting radiation from the sample, the radiation from the sample including at least one of radiation elastically scattered by one or more defects of the sample or photoluminescence radiation emitted by the one or more photoluminescing defects of the sample;
separating the radiation from the sample into a first portion of radiation including one or more wavelengths in the visible spectrum associated with the light emitted by the one or more photoluminescing defects of the sample, a second portion of radiation including the normal-illumination wavelength light, and at least a third portion of radiation including the oblique-illumination wavelength light;
measuring one or more characteristics of at least one of the first portion of radiation, the second portion of radiation and the third portion of radiation;
detecting one or more scattering defects based on the measured one or more characteristics of at least one of the second portion of radiation and the third portion of radiation; and
detecting one or more photoluminescence defects based on the measured one or more characteristics of at least one of the first portion of radiation, the second portion of radiation and the third portion of radiation by comparing the one or more characteristics of at least one of the first portion of radiation, the second portion of radiation and the third portion of radiation acquired from an area of the sample absent of photoluminescing defects to one or more characteristics of at least one of the first portion of radiation, the second portion of radiation and the third portion of radiation acquired from a measured region of the sample.

59. A method for defect detection and photoluminescence measurement of a sample comprising:
directing a beam of oblique-illumination wavelength light onto a portion of the sample along a direction oblique to the surface of the sample;
directing a beam of normal-illumination wavelength light along a direction substantially normal to the surface of the sample, wherein the beam of light of the normal-illumination wavelength is suitable for causing one or more photoluminescing defects of the sample to emit photoluminescent light;
collecting radiation from the sample, the radiation from the sample including at least one of radiation elastically scattered by one or more defects of the sample or photoluminescence radiation emitted by the one or more photoluminescing defects of the sample;

separating the radiation from the sample into a first portion of radiation including one or more wavelengths in the visible or near-infrared spectrum associated with the light emitted by the one or more photoluminescing defects of the sample, a second portion of radiation including the normal-illumination wavelength, a third portion of radiation including the oblique-illumination wavelength and at least a fourth portion of radiation including one or more wavelengths in the ultraviolet spectrum associated with the photoluminescent light emitted by the one or more photoluminescing defects of the sample;

measuring one or more characteristics of at least one of the first portion of radiation, one or more characteristics of the second portion of radiation, one or more characteristics of the third portion of radiation and one or more characteristics of the fourth portion of radiation;

detecting one or more scattering defects based on the measured one or more characteristics of at least one of the second portion of radiation and the third portion of radiation; and detecting one or more photoluminescence defects based on the measured one or more characteristics of at least one of the first portion of radiation, the second portion of radiation, the third portion of radiation by comparing the one or more characteristics of at least one of the first portion of radiation, the second portion of radiation, the third portion of radiation and the fourth portion of radiation acquired from an area of the sample absent of photoluminescing defects to one or more characteristics of at least one of the first portion of radiation, the second portion of radiation, the third portion of radiation and the fourth portion of radiation acquired from a measured region of the sample.

60. A method for defect detection and photoluminescence measurement of a sample comprising:
   directing a beam of normal-illumination wavelength light along a direction substantially normal to the surface of the sample, wherein the beam of light of the normal-illumination wavelength is suitable for causing one or more photoluminescing defects of the sample to emit photoluminescent light;
   collecting radiation from the sample, the radiation from the sample including at least one of radiation elastically scattered by one or more defects of the sample or photoluminescence radiation emitted by the one or more photoluminescing defects of the sample;
   separating the radiation from the sample into a first portion of radiation including one or more wavelengths in the visible or near-infrared spectrum associated with the light emitted by the one or more photoluminescing defects of the sample, a second portion of radiation including the normal-illumination wavelength and at least a third portion of radiation including one or more wavelengths in the ultraviolet spectrum associated with the photoluminescent light emitted by the one or more photoluminescing defects of the sample;
   measuring one or more characteristics of at least one of the first portion of radiation, one or more characteristics of the second portion of radiation and one or more characteristics of the third portion of radiation;
   detecting one or more scattering defects based on the measured one or more characteristics of at least one of the second portion of radiation and the third portion of radiation; and
   detecting one or more photoluminescence defects based on the measured one or more characteristics of at least one of the first portion of radiation, the second portion of radiation, and the third portion of radiation by comparing the one or more characteristics of at least one of the first portion of radiation, the second portion of radiation and the third portion of radiation acquired from an area of the sample absent of photoluminescing defects to one or more characteristics of at least one of the first portion of radiation, the second portion of radiation and the third portion of radiation acquired from a measured region of the sample.

61. A method for defect detection and photoluminescence measurement of a sample comprising:
   directing a beam of normal-illumination wavelength light onto a portion of the sample along a direction substantially normal to the surface of the sample, wherein the beam of light of the normal-illumination wavelength is suitable for causing one or more photoluminescing defects of the sample to emit photoluminescent light;
   collecting radiation from the sample, the radiation from the sample including at least one of radiation elastically scattered by one or more defects of the sample or photoluminescence radiation emitted by the one or more photoluminescing defects of the sample;
   separating the radiation from the sample into a plurality of portions of photoluminescent radiation, each portion including one or more wavelengths in a different spectral range of the light emitted by the one or more photoluminescing defects of the sample;
   measuring one or more characteristics of each of the plurality of portions of photoluminescent radiation;
   detecting one or more photoluminescence defects based on the measured one or more characteristics of each of the plurality of portions of photoluminescent radiation; and
   classifying the one or more detected photoluminescence defects based on one or more signals associated with each of the plurality of portions of photoluminescent radiation.

62. A method for defect detection and photoluminescence measurement of a sample comprising:
   directing a beam of normal-illumination wavelength light onto a portion of the sample along a direction substantially normal to the surface of the sample, wherein the beam of light of the normal-illumination wavelength is suitable for causing one or more photoluminescing defects of the sample to emit photoluminescent light;
   directing a beam of oblique-illumination wavelength light onto a portion of the sample along a direction oblique to the surface of the sample;
   collecting radiation from the sample, the radiation from the sample including at least one of radiation elastically scattered by one or more defects of the sample or photoluminescence radiation emitted by the one or more photoluminescing defects of the sample;
   separating the radiation from the sample into a visible portion of photoluminescent radiation and a near ultraviolet (NUV) portion of photoluminescent radiation;
   measuring one or more characteristics of the visible portion of photoluminescent radiation and the NUV portion of photoluminescent radiation;
   detecting one or more photoluminescence defects based on the measured one or more characteristics of the visible portion of photoluminescent radiation and the NUV portion of photoluminescent radiation; and
   classifying the one or more detected photoluminescence defects based on one or more signals associated with the visible portion of photoluminescent radiation and the NUV portion of photoluminescent radiation.

* * * * *